(12) United States Patent
Wu et al.

(10) Patent No.: US 12,312,591 B2
(45) Date of Patent: May 27, 2025

(54) METHODS AND SYSTEMS FOR GENERATING COMPLEX SPATIAL PATTERNS

(71) Applicants: Fuqing Wu, Tempe, AZ (US); Samat Bayakhmetov, Tempe, AZ (US); Changhan He, Tempe, AZ (US); Qi Zhang, Tempe, AZ (US); Xingwen Chen, Tempe, AZ (US); Yang Kuang, Tempe, AZ (US); Xiao Wang, Chandler, AZ (US)

(72) Inventors: Fuqing Wu, Tempe, AZ (US); Samat Bayakhmetov, Tempe, AZ (US); Changhan He, Tempe, AZ (US); Qi Zhang, Tempe, AZ (US); Xingwen Chen, Tempe, AZ (US); Yang Kuang, Tempe, AZ (US); Xiao Wang, Chandler, AZ (US)

(73) Assignee: Arizona Board of Regents on Behalf of Arizona, Scottsdale, AZ (US)

( * ) Notice: Subject to any disclaimer, the term of this patent is extended or adjusted under 35 U.S.C. 154(b) by 980 days.

(21) Appl. No.: 17/382,305

(22) Filed: Jul. 21, 2021

(65) Prior Publication Data
US 2022/0025385 A1  Jan. 27, 2022

Related U.S. Application Data

(60) Provisional application No. 63/055,321, filed on Jul. 22, 2020.

(51) Int. Cl.
*C12N 15/72* (2006.01)
*C12Q 1/6897* (2018.01)

(52) U.S. Cl.
CPC .......... *C12N 15/72* (2013.01); *C12Q 1/6897* (2013.01); *C12N 2800/101* (2013.01); *C12N 2830/002* (2013.01); *C12N 2830/003* (2013.01)

(58) Field of Classification Search
CPC .............. C12N 15/72; C12N 2800/101; C12N 2830/002; C12N 2830/003; C12Q 1/6897
See application file for complete search history.

(56) References Cited

PUBLICATIONS

Wu et al., "A Synthetic Biology Approach to Sequential Stripe Patterning and Somitogenesis", p. 1-19, Oct. 2019.*
Wu et al., "A Synthetic Biology Approach to Sequential Stripe Patterning and Somitogenesis", p. 1-19, Oct. 2019—Supplementary Materials.*
B. Munsky, G. Neuert, A. van Oudenaarden, Using Gene Expression Noise to Understand Gene Regulation. Science. 336, 183-187 (2012).
F. Wu, D. J. Menn, X. Wang, Quorum-sensing crosstalk-driven synthetic circuits: from unimodality to trimodality. Chem. Biol. 21, 1629-1638 (2014).
J. M. Raser, E. K. O'Shea, Noise in Gene Expression: Origins, Consequences, and Control. Science. 309, 2010-2013 (2005).
J. W. Young et al., Measuring single-cell gene expression dynamics in bacteria using fluorescence time-lapse microscopy. Nat. Protoc. 7, 80-88 (2011).
K. D. Litcofsky, R. B. Afeyan, R. J. Krom, A. S. Khalil, J. J. Collins, Iterative plug-andplay methodology for constructing and modifying synthetic gene networks. Nat. Methods. 9, 1077-1080 (2012).
L. Marcon, X. Diego, J. Sharpe, P. Muller, High-throughput mathematical analysis identifies Turing networks for patterning with equally diffusing signals. eLife. 5, e14022 (2016).
P. S. Stewart, Diffusion in Biofilms. J. Bacteriol. 185, 1485-1491 (2003).
Q. Ouyang, R. Li, G. Li, H. L. Swinney, Dependence of Turing pattern wavelength on diffusion rate. J. Chem. Phys. 102, 2551-2555 (1995).

* cited by examiner

*Primary Examiner* — Nelson B Moseley, II
(74) *Attorney, Agent, or Firm* — FULLER IP LAW LLC; Rodney J. Fuller

(57) ABSTRACT

Synthetic gene circuits and methods for modeling complex spatial patterns (for example, in somitogenesis) and related plasmids are disclosed herein. Also disclosed herein are methods of generating an expression pattern using the synthetic gene circuit described herein.

20 Claims, 11 Drawing Sheets
(11 of 11 Drawing Sheet(s) Filed in Color)

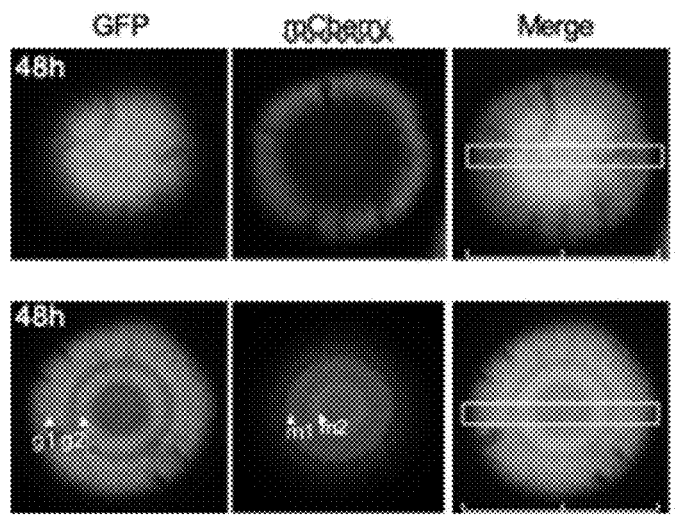
FIG. 3A
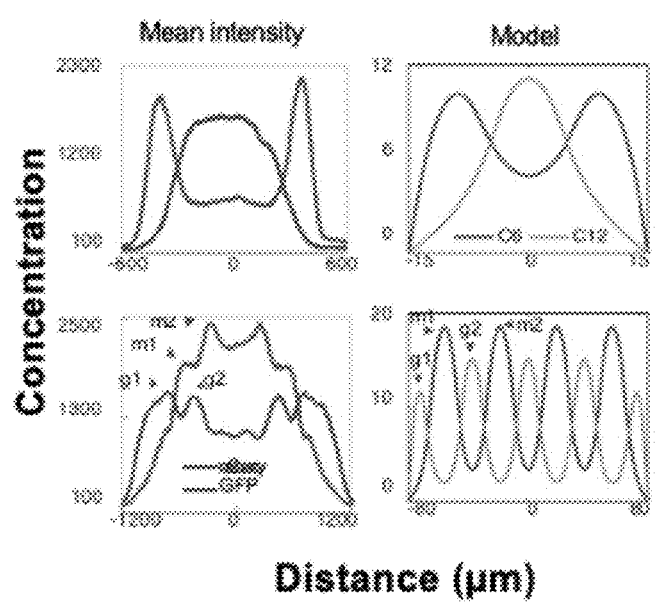
FIG. 3B
FIG. 3C
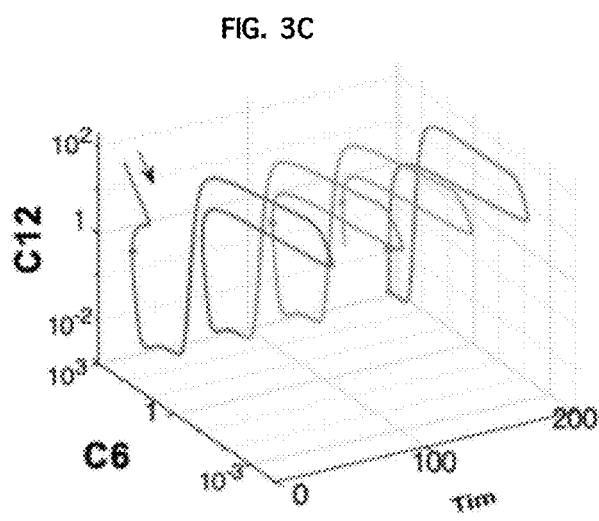
FIG. 3D
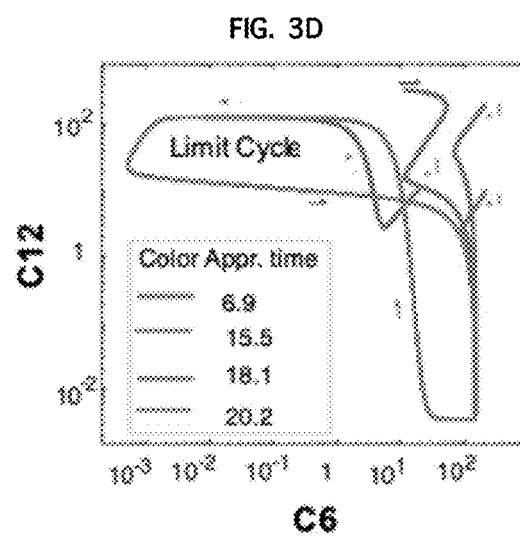

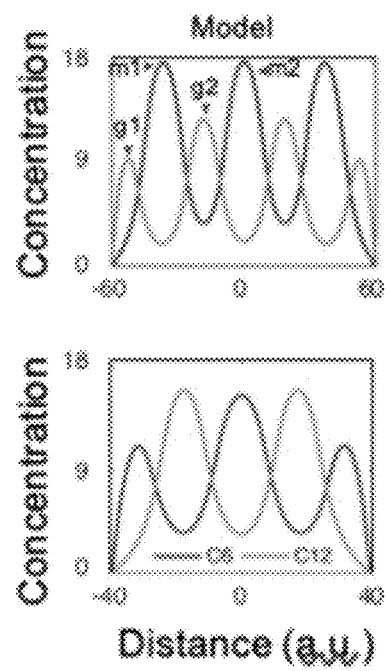
FIG. 4A
FIG. 4B
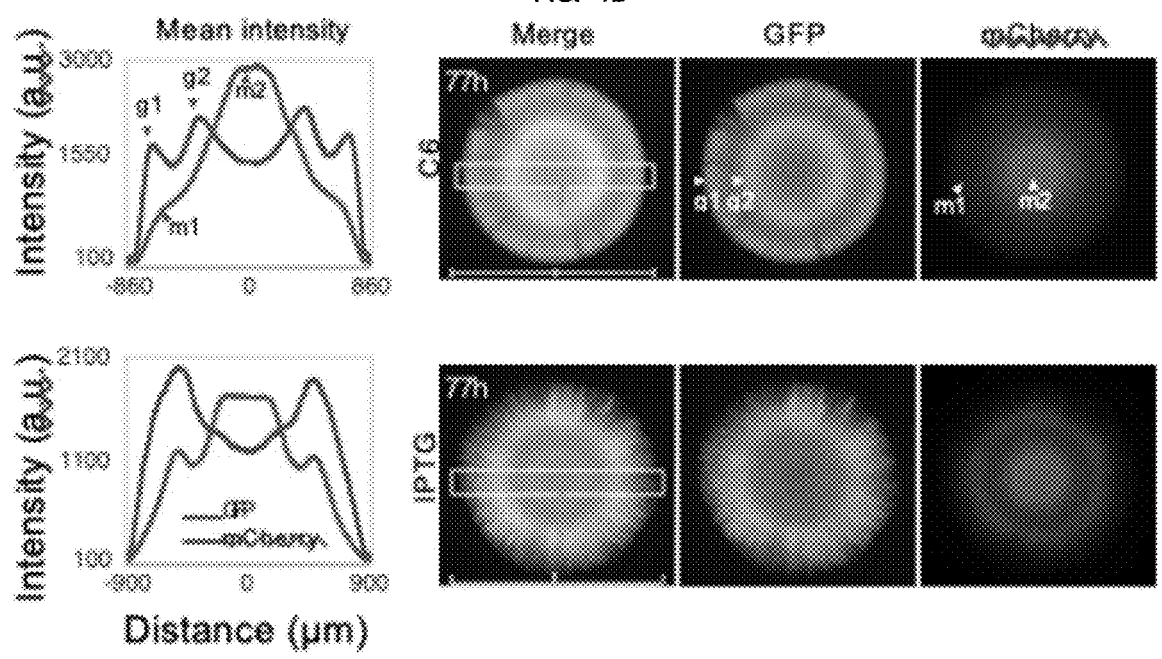

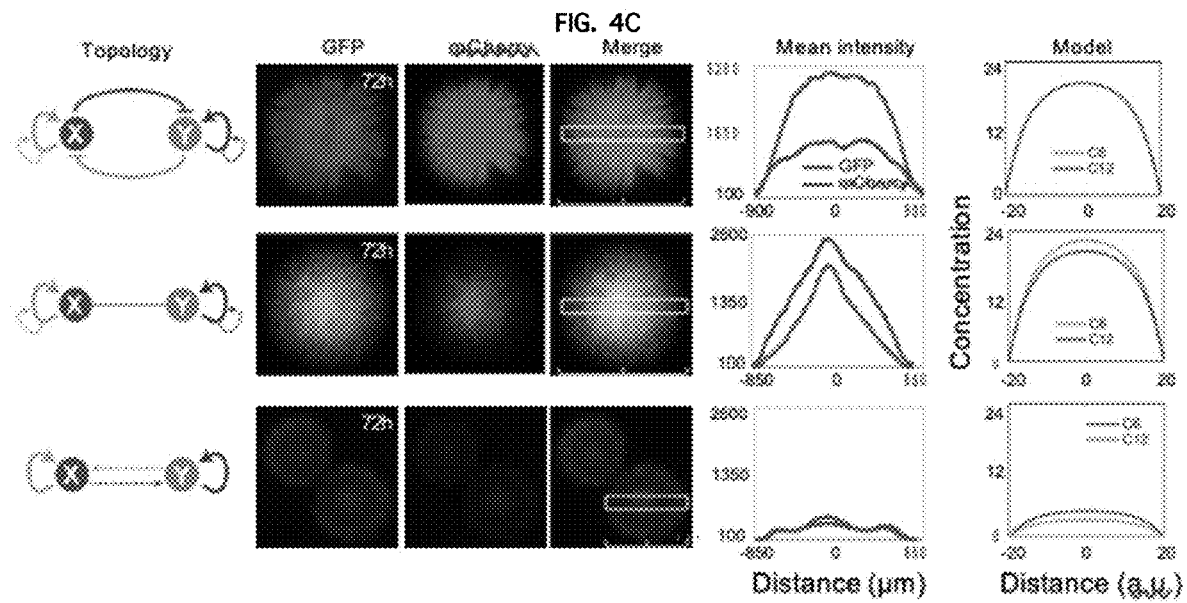
FIG. 4C
FIG. 5A
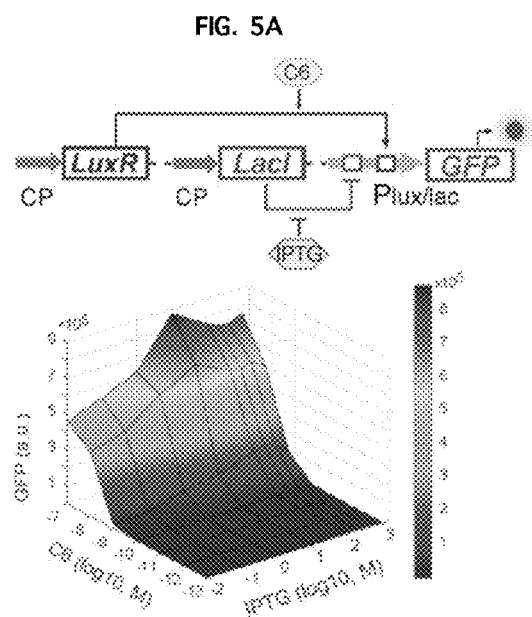
FIG. 5B
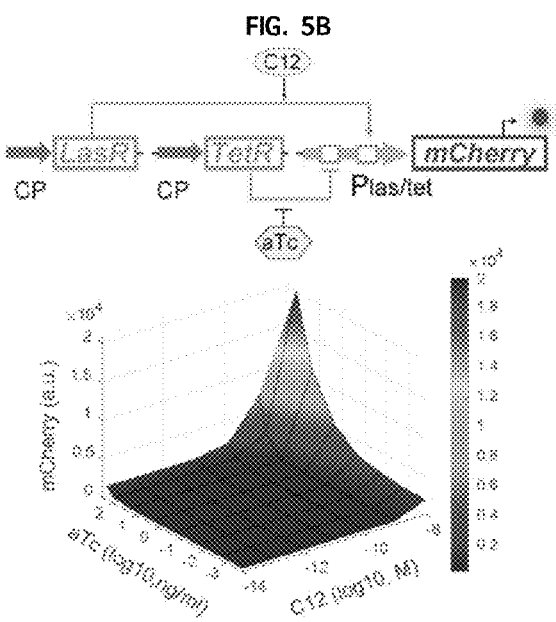

FIG. 6
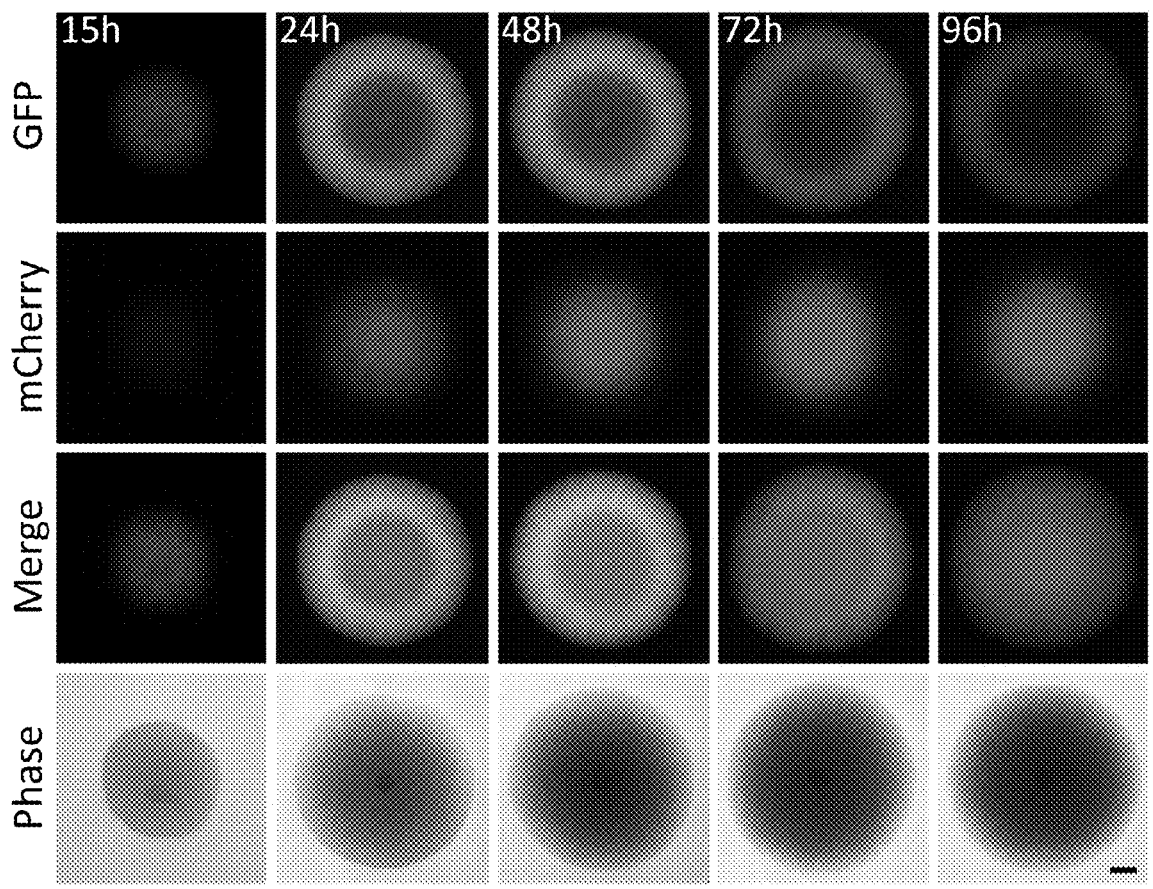
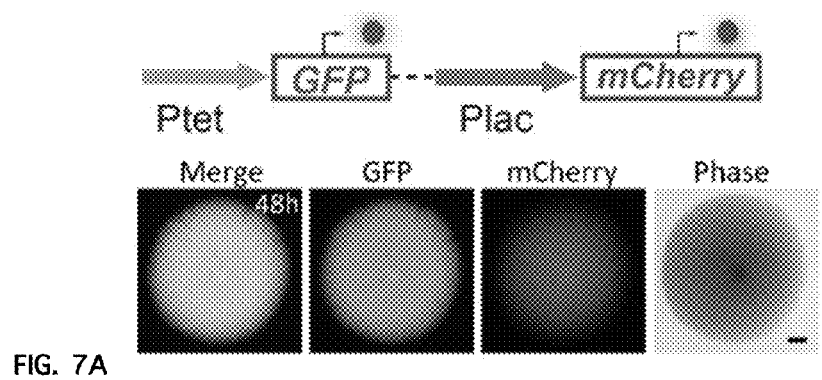
FIG. 7A
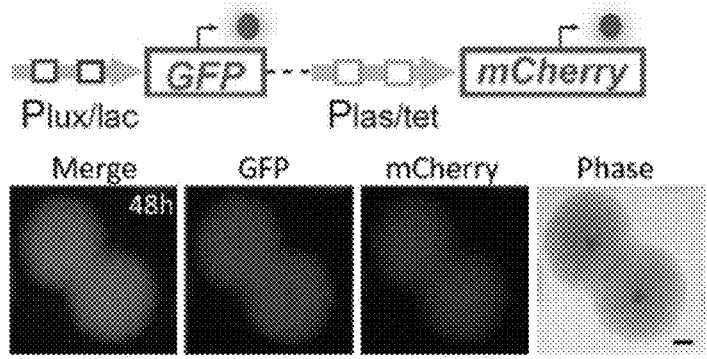
FIG. 7B

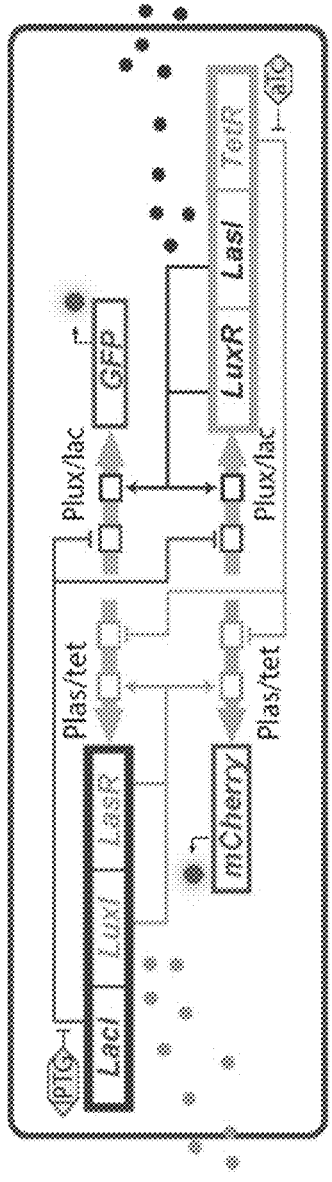 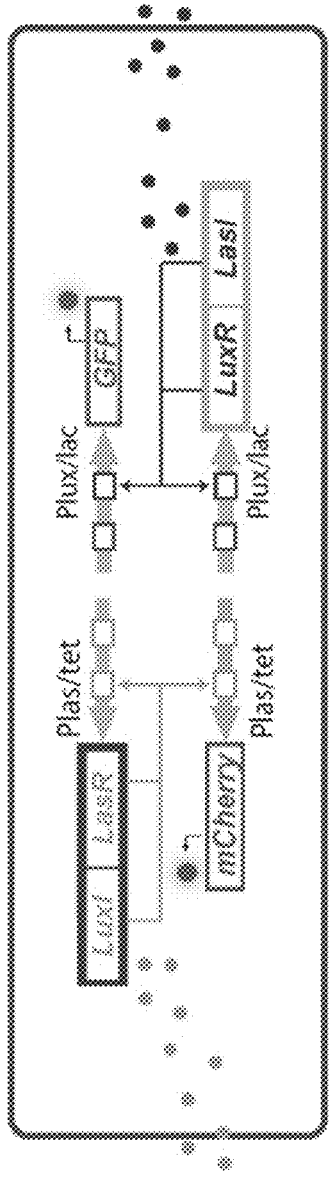 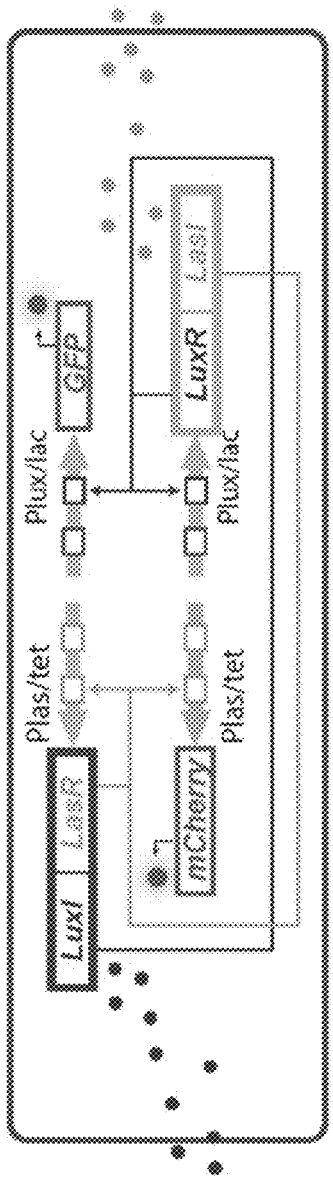
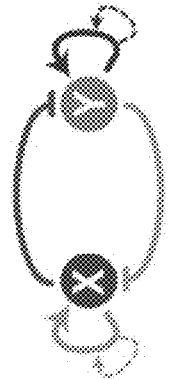 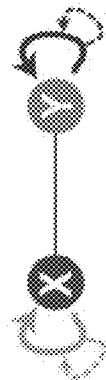 
FIG. 11A     FIG. 11B     FIG. 11C

METHODS AND SYSTEMS FOR GENERATING COMPLEX SPATIAL PATTERNS

CROSS-REFERENCE TO RELATED APPLICATIONS

This application claims the benefit of U.S. provisional patent application 63/055,321, filed Jul. 22, 2020, the contents of which are hereby incorporated by reference in its entirety.

STATEMENT REGARDING FEDERALLY SPONSORED RESEARCH

This invention was made with government support under 1100309 awarded by the National Science Foundation. The government has certain rights in the invention.

TECHNICAL FIELD

The present disclosure relates to a synthetic biology approach to generate complex spatial patterns from a reaction diffusion circuit motif.

BACKGROUND

Reaction-diffusion (RD) based clock and wavefront model has long been proposed as the mechanism underlying biological pattern formation of repeated and segmented structures including somitogenesis. Turing's seminal work first proposed RD as the "chemical basis of morphogenesis" over six decades ago. It provides a general theoretical foundation of pattern formation via RD mechanisms. Two decades later, RD driven clock and wavefront (CW) mechanism was hypothesized as the mechanism underlying formation of repeated and segmented structures such as somites in development. Since then, RD driven pattern formation has been demonstrated or identified in chemical, physical, and ecological systems. However, its much-hypothesized role in multicellular pattern formation has not been fully studied biologically. Systematic molecular level understanding of the mechanism remains elusive largely due to the lack of suitable experimental systems to probe RD quantitatively in vivo. For example, somite development requires precise temporal and spatial coordination between a heterogeneous web of intracellular responses and intercellular communications, both under control of complex gene regulation networks and influences of universal gene expression stochasticity. Such complexity poses a great challenge to fully understand mechanistic basis of somite formation in vivo. Engineered microbes carrying rationally designed gene circuits provide an effective venue to study this problem from bottom up. Previous studies using synthetic circuits have demonstrated formation of predefined patterns, cell motility-based stripe formation, and scale invariant ring pattern formation. However, gene network directed RD based clock and wavefront pattern formation, despite its importance in developmental biology and extensive theoretical studies, has not been experimentally realized.

SUMMARY

Described herein is a synthetic gene circuit that couple gene expression regulation (reaction) with quorum sensing (diffusion) to guide self-organizing bacterial cells into stripe patterns at both microscopic and colony scales and plasmids that make the synthetic gene circuit. In some aspects, the gene circuit comprises two plasmids. Each plasmid comprises a Plas/tet promoter, a Plux/lac promoter, a reporter gene, and a combination of genes, wherein the Plas/tet promoter drives the expression of the reporter gene or the combination of genes; and the Plux/lac promoter drives the expression of the reporter gene or the combination of genes. In certain embodiments, the Plas/tet promoter drives the expression of the reporter gene, while the Plux/lac promoter drives the expression of the combination of genes. In other embodiments, the Plas/tet promoter drives the expression of the combination of genes, while the Plux/lac promoter drives the expression of the reporter gene.

The combination of genes is selected from the group consisting of: LacI, LuxI, LasR, LuxR, LasI, and TetR. In some aspects, the comprises at least two genes. In some embodiments, the combination of genes comprises LuxI or LuxR and LasR or LasI, for example, LuxI and Las R or LuxR and Las I. In other embodiments, the combination of genes comprises LacI or LuxR, LuxI or LasI; and LasR or TetR. In an exemplary embodiment, the combination of genes comprises LacI, LuxI, and LasR. In another exemplary embodiment, the combination of genes comprises LuxR, LasI, and TetR.

In the synthetic gene circuit, comprises a first plasmid (which comprises a first hybrid promoter, a second hybrid promoter, a first reporter gene, and a first combination of genes) and a second plasmid (which comprises a third hybrid promoter, a fourth hybrid promoter, a second reporter gene, and a second combination of genes). The first hybrid promoter is activated by a first gene and inhibited by a second gene. The second hybrid promoter is activated by a third gene, inhibited by a fourth gene, drives the expression of the first reporter gene. The first combination of genes comprising the first gene, the fourth gene, and a first autoinducer synthase gene. The third hybrid promoter is activated by the first gene and inhibited by the second gene. The fourth hybrid promoter is activated by the third gene and inhibited by the fourth gene. The third hybrid promoter drives the expression of the second reporter gene. The second combination of genes comprises the second gene, the third gene, and a second autoinducer synthase gene. The first hybrid promoter and the third hybrid promoter are the same hybrid promoters, while the second hybrid promoter and the fourth hybrid promoter are the same hybrid promoters. However, the first reporter gene and the second reporter gene are different, and the first autoinducer synthase gene and the second autoinducer synthase gene are different. The product of the first autoinducer synthase gene forms a complex with the product of the first gene to activate the third hybrid promoter and the third hybrid promoter, and the product of the second autoinducer synthase gene forms a complex with the product of the third gene to activate the second hybrid promoter and the fourth hybrid promoter.

Experimentally verified mathematical model confirms that these periodic spatial structures are emerged from the integration of oscillatory gene expression as the molecular clock and the outward expanding diffusions as the propagating wavefront. Furthermore, the paired model experiment data illustrate that the RD-based patterning is sensitive to initial conditions and can be modulated by external inducers to generate diverse patterns, including multiple stripe pattern, target-like pattern, and ring patterns with reversed fluorescence.

The described synthetic gene circuit, with tests on different topologies of gene networks, demonstrate that network motifs enabling robust oscillations are foundations of sequential stripe pattern formation. These results verified close connections between gene network topology and resulting RD driven pattern formation, which demonstrate the described synthetic gene circuit provides an engineering approach to help understand biological development.

Also described herein are methods of generating an expression pattern of a gene with a synthetic gene circuit. The methods comprise introducing into a cell a synthetic gene circuit described herein to produce an altered cell and providing to the altered cell a first inducer compound that is an inducer for the second autoinducer synthase gene, whereby the altered cell expresses the first reporter gene in a ring pattern. In some implementations, a compound that alters the strength of the mutual modulation in the synthetic gene circuit is provided to the altered cell to modulate the complexity of the ring patterned expression of the first reporter gene, for example, resulting in a striped or target pattern of expression. In some embodiments, the cell is a prokaryotic cell, for example $E.\ coli$. In other embodiments, the cell is a eukaryotic cell.

Additionally, methods of determining the pattern formation of a synthetic gene circuit are disclosed. In one embodiment, the method comprises first defining a partial differential equation (PDE) model based on a reaction-diffusion process within the synthetic gene circuit. The PDE model comprises a plurality of equations each modeling a biochemical reaction within the synthetic gene circuit, gene activation and gene repression being represented as hill functions, wherein the equations each comprise a plurality of coefficients each representing one of promoter basal expression, feedback, protein production, protein degradation, activation rate, and repression rate. For instance, equations 7-12 of the Examples. The method also comprises defining a set of boundary conditions and a set of initial conditions for the reaction-diffusion model based upon at least one topology of the synthetic gene circuit, a plurality of biologically feasible coefficient values, and an external perturbation and determining a pattern expression dynamic for the synthetic gene circuit by numerically solving the PDE model.

The foregoing and other aspects, features, and advantages will be apparent to those artisans of ordinary skill in the art from the DESCRIPTION and DRAWINGS, and from the CLAIMS.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A show an experimental design of the MINPAC network. Plas/tet (pink arrow) can be activated by LasR (yellow) and repressed by TetR (light green), while Plux/lac (green arrow) can be activated by LuxR (blue) and repressed by LacI (red). LuxI (blue) synthesizes C6 (blue dots) to bind with LuxR to activate pLux/lac, while LasI (yellow) synthesizes C12 (yellow dots) to bind with LasR to activate Plas/tet. GFP and mCherry serve as reporters for Plux/lac and Plas/tet. FIG. 1B is an abstract diagram of MINPAC topology, where X and Y mutually inhibit each other (T-bars) and auto-activate (arrowheads) itself, meanwhile X and Y can mutually activate through small autoinducer mediated intercellular communication (dashed arrowheads). Genes and regulations are color-coded corresponding to the circuit in FIG. 1A. FIG. 1C is an illustration of an exemplary ring pattern forming from a single $E.\ coli$ cell harboring MINPAC circuit. FIG. 1D depicts MINPAC directing single cells to self-organize into ring pattern at microscopic scale. Representative experiments of pattern formation from a single cell to colony by time-lapse microscopy (Scale bar represents 5 μm). The 21-hour image is captured and combined by four individual images. FIG. 1E shows that MINPAC cells self-organized to form double-ring pattern at colony scale. Representative fluorescence images were taken at 48 hr. Magnification: 2×. FIG. 1 shows the mean fluorescence intensity across the center of pattern-generating colony (the white box in FIG. 1E). Distance indicates the size of the colony. FIG. 1G depicts the PDE model simulations. The left graph shows the extracellular C6 and C12 concentrations, which are corresponding to mCherry and GFP intensities, respectively. The right graph is a two-dimensional ring pattern simulated from the model, with high C6 concentration (red) for cells in the core and high C12 concentration (green) on the edge of the colony, forming a similar double-ring pattern as in FIG. 1E.

FIG. 2A is an illustration of the MINPAC composition of two symmetric positive plus-negative oscillator motifs. Parameter τ is used to describe the strength of one negative feedback (node Y inhibits node X). FIGS. 1B and 1C are model comparison between one-motif topology and two motif MINPAC. Oscillation from one-motif topology is highly dependent on the parameter τ (FIG. 2B), whereas MINPAC harbors a greater robustness and amplitude against parameter τ changes to generate temporal oscillation (FIG. 2C). Cyan and yellow colormaps represent the C6 and C12 concentrations, respectively. The red and blue solid lines are C6 and C12 concentrations when τ equals to 0 (i.e. no negative feedback). FIG. 1D is a diagram of an exemplary growing colony. Circles with different colors indicate the colony position at different time points. Center is labeled as o, and d is the distance to the center of the colony. FIG. 1E shows the normalized external C12 concentration, directly correlated with experimental GFP intensities, of a pattern-growing colony with time and space from the PDE model simulation. Starting from the center of a colony, colored curves represent C12 concentrations along the colony radius at different time points. Grey arrows indicate the traveling direction of the wave front. FIG. 2F depicts a time course of a growing colony having multiple GFP rings. FIG. 2G is a quantified temporal and spatial fluorescence intensities of the multiple GFP ring forming colony in FIG. 2F, showing similar dynamics to model simulation in FIG. 2E. The distance starts from center of the colony from 16 hr to 132 hr. Each pixel is 3.22 μm.

FIGS. 3A-3D depict, in accordance with certain embodiments, initial conditions and associated approaching time led to diverse patterns. FIG. 3A shows two observations distinct to FIG. 1E generated by MINPAC circuit. The top row of images shows a ring pattern with a GFP core and a mCherry outer ring; the bottom row of images shows a multiple GFP-mCherry ring pattern. FIG. 3B shows the mean fluorescence intensities across the center of the ring-forming colonies in FIG. 3A (left), and model simulations recapitulate experimental patterns only through changing the initial conditions of the model (right). For the mean fluorescence intensities graph, the rings of FIG. 3A correspond to the peaks and are labeled. FIG. 3C depicts an exemplary trajectory of a random initial point (black arrow) going to oscillation periods (red, green and yellow curves) simulated from MINPAC reaction term. The grey "butterfly" curve illustrates the limit cycle. FIG. 3D depicts the approaching time for different initial conditions. Colored curve shows the trajectory before stable oscillations and the approaching time is calculated for the solution going from its starting point to the stable limit cycle (grey curve).

FIGS. 4A-4C show, in accordance with certain embodiments, MINPAC-directed patterning is tunable and intrinsic to its network topology. FIG. 4A depicts model predictions of the pattern under external inducers C6 (top) and IPTG (bottom). FIG. 4B shows the experimental validations for model predictions, with C6 and IPTG induction. The top row of images shows two GFP rings were observed experimentally under 10-8 M C6 induction at 77 hr. Its mean fluorescence intensity across the colony is similar to model prediction (FIG. 4A, top). The bottom row of images of FIG. 4B shows that a target-like mCherry ring and an outer GFP ring were observed under 10 μM IPTG induction. The mean fluorescence intensity is consistent to model prediction (FIG. 4A, bottom). Time course of pattern generation can be found in FIG. 10B. FIG. 4C shows the three control circuits' topology and directed patterns (mean fluorescence intensities across the center of the ring patterns and model simulations). The three circuits are constructed with the same molecular components in MINAPC. The top row are results for a perturbed MINPAC topology where the intercellular X-Y communications are replaced by intercellular auto-activation of X and Y. No specific pattern is observed experimentally. The middle row are results for a topology where mutual inhibition is removed and communication is replaced by intercellular auto-activation of X and Y. Strong GFP and mCherry are simultaneously expressed and merged fluorescence is yellow. The bottom row are results for a topology where all regulatory edges are kept but the mutual inhibition module is removed. A weak yellow core and outer ring is observed. The model simulations of the three control circuits show consistency with experimental results.

FIGS. 5A and 5B depict, in accordance with certain embodiments, the results of promoter functionality test. The top images of FIGS. 5A and 5B show the circuit construction. FIG. 5A relates to a biological circuit that test hybrid promoter Plux/lac. LuxR and LacI are individually expressed from a constitutive promoter (CP) to regulate Plux/lac transcription. GFP is a reporter of Plux/lac, and maximum GFP can be achieved with the presence of IPTG and C6. The bottom image of FIG. 5A depicts experimental data (12 hrs) showing GFP response to doses of C6 and IPTG induction. FIG. 5B relates to a biological circuit that test promoter Plas/tet. The bottom image of FIG. 5B depict data (24 hrs) showing Plas/tet is only activated in the presence of C12 and aTc. mCherry is a reporter of Plas/tet activity. Fluorescence was measured by flow cytometry after adding the inducers. Each data point was averaged from three repeated experiments.

FIG. 6 depicts, in accordance with certain embodiments, a time course for the MINPAC-directed ring pattern formation under no inductions. Scale bar represents 100 μm. Magnification: 2×.

FIGS. 7A and 7B depict, in accordance with certain embodiments, pattern formation from negative control circuits. FIG. 7A relates to a circuit with GFP and mCherry expressed from constitutive promoters. High GFP and mCherry simultaneously expressed and a yellow fluorescence disk is observed at 48 hours. Scar bar: 100 μm. FIG. 7B relates to a circuit with GFP and mCherry expressed from hybrid promoters Plux/lac and Plas/tet. No obvious ring patterns were observed at 48 hrs.

FIG. 9A is an abstract diagram of MINPAC topology, which is composed of two symmetric classical positive-plus-negative oscillator topologies. Parameters $k_1$, $k_2$, $k_3$, $k_4$ are production rates for each edge of the MINPAC motif; and $\tau_1$, and $\tau_2$ are the inhibition strength of the two negative feedbacks. FIG. 9B shows that MINPAC quickly goes to stable steady states when all the corresponding parameters are fully symmetric, i.e. $k_1$ equals to $k_2$; $k_3$ equals to $k_4$, and $\tau_1$ equals to $\tau_2$. Similar applications to all the other parameters. FIGS. 9C-9E show that oscillation emerged when there is a tiny asymmetry between the two symmetric motifs. Keeping all the other parameters unchanged, MINPAC rapidly goes to robust and stable oscillation periods when $k_1$ increases by 0.8% (i.e. $k_1=1.008*k_2$) or $k_3$ increases by 8.75% (i.e. $k_3=1.0875*k_4$) or $\tau_1$ increases by 1% (i.e. $\tau_{1=1.01}*\tau_2$). This is also applied to the cases when decreasing parameters in a small scale, which is another way to introduce the asymmetry.

FIG. 10A depicts time course results for the MINPAC directed pattern formation with external C6 (top) and IPTG (bottom) inductions. FIGS. 10B and 10C show a model prediction (left), its corresponding experimental validation (right), and mean fluorescence intensities (middle). FIG. 10B relates to pattern formation under C12 induction. Both model and experiments showed that $10^{-9}$ M C12 induction resulted in two GFP rings with unbalanced intensities. FIG. 10C predicts a dominant mCherry expression under aTc induction, and the experimental result confirmed the model prediction that only mCherry is expressed under 2 ng/ml aTc induction.

FIGS. 11A-11C depict, in accordance with certain embodiments, topology and experimental design for the three MINPAC control circuits. FIG. 11A relates to a perturbed MINPAC topology. The intercellular X-Y communications are replaced by intercellular auto-activation of X and Y. FIG. 11B relates to a topology where mutual inhibition is removed, and communication is replaced by intercellular auto-activation of X and Y. FIG. 11C relates to a MINPAC sub-network, having all regulatory edges of MINPAC, except the mutual inhibition module. The right side are the experimental designs for each control circuit, which is engineered with the same bio-components as in the MINPAC. Genes, promoters, and regulations are color-coded corresponding to the topology on the left side.

DETAILED DESCRIPTION

Figure 1A:
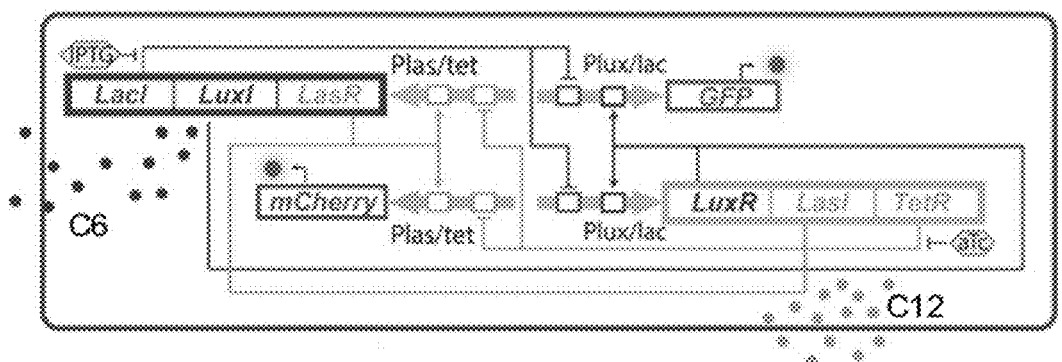
FIGS. 1A-1G depict, in accordance with certain embodiments, a conceptual and experimental design of a mutually inhibitory network with positive autoregulation and communications (MINPAC) and reaction-diffusion based pattern formation.

Detailed aspects and applications of the disclosure are described below in the drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that the present technology may be practiced without these specific details. It should be noted that there are many different and alternative configurations, devices and technologies to which the disclosed technologies may be applied. The full scope of the technology is not limited to the examples that are described below.

The singular forms "a," "an," and "the" include plural referents unless the context clearly dictates otherwise. Thus, for example, reference to "a step" includes reference to one or more of such steps.

Past studies have suggested that nonlinear multistable systems could also direct spatiotemporal pattern formation when coupled with external diffusion process. Following this strategy to achieve a multicellular pattern formation, a mutually inhibitory network with positive autoregulation and communications (MINPAC) was designed and constructed. The disclosure demonstrates a bottom-up synthetic biology approach to generate complex spatial patterns arising from well-designed reaction-diffusion circuit motif and integrates experimental data with analytical framework across time and spatial scales to shed lights on the molecular mechanisms of somitogenesis and biological pattern formation. Accordingly, the synthetic gene circuits and methods described herein are tools for bettering the understanding of natural developmental processes and facilitating the engineering of synthetic tissues. Understanding the mechanisms of biological pattern formation also facilitates engineering of more complex biofuel cells, improves the development of organ or tissue engineering, and enables initiation of site-specific biological processes, such as wound healing.

Figure 1B:
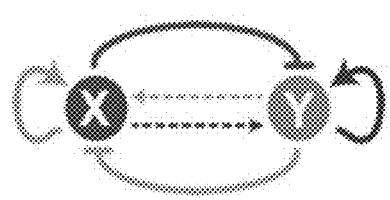

MINPAC is a synthetic gene circuit that couple gene expression regulation (reaction) with quorum sensing (diffusion) based on previously demonstrated quadrastable gene circuit, though with the addition quorum-sensing modules to enable intercellular communications (FIGS. 1A and 1B). MINPAC is capable of directing engineered single cells to form self-organized tunable patterns with multiple rings. MINPAC is a complete motif composed of intracellular transcriptional network and intercellular communication modules, both of which cross-regulate each other to direct spatial pattern formation involving the coordination of molecular gene expression, cellular population response, and positional information interpretation. Similar natural counterparts of MINPAC design can be found in the interaction networks of gap genes for the anterior-posterior axis patterning in Drosophila.

MINPAC comprises two plasmids, each comprising two hybrid promoters Plas/tet and Plux/lac, a reporter gene, and a combination of genes selected from the group consisting of: LacI, LuxI, LasR, LuxR, LasI, and TetR. The hybrid promoter Plas/tet is activated by LasR-C12 complex but inhibited by TetR protein. The hybrid promoter Plux/lac is activated by LuxR-C6 complex but inhibited by LacI protein. The two plasmids along with their hybrid promoters harbor high nonlinearity and inducibility (FIGS. 1A, 5A and 5B). LasI and LuxI are synthases that catalyze the synthesis of autoinducer 3-oxo-C12-HSL (C12) and 3-oxo-C6-HSL (C6), respectively. The two small autoinducers diffuse out of and into cells to mediate cell-cell communication and coordinate population behaviors on a spatial domain. LasR and Lux activate Plas/tet and Plux/lac in the presence of C12 and C6, respectively, forming positive autoregulation. IPTG inhibits the repressive effect of LacI on Plux/lac, and aTc counteracts TetR inhibition on Plas/tet, forming the mutual inhibitions.

In the first plasmid (also referred to herein as "node X"), the Plux/lac promoter drives the expression of a reporter gene, while in the second plasmid (also referred to herein as "node Y"), the expression of another reporter gene is driven by the Plas/tet promoter. The reporter gene in each of the plasmids differs (see, for example, FIG. 1A). Accordingly, in some aspects, the disclosure relates to a plasmid comprising a Plas/tet promoter, a Plux/lac promoter, a report gene, and a combination of genes selected from the group consisting: LacI, LuxI, LasR, LuxR, LasI, and TetR. In some aspects, the reporter gene is a gene that encodes a fluorescent protein, for example, mCherry or green fluorescent protein (GFP). In other aspects, the reporter gene may be any gene where it would be desirable to control the site of its expression.

The combination of genes comprises at least two genes. In one embodiment, the combination of genes comprises LacI, LuxI, and LasR. In another embodiment, the combination of genes comprises LuxR, LasI, TetR. The expression of the combination of genes is not driven by a promoter that is neither activated or inhibited with the products of the combination of genes (for example, the expression of LasR or TetR is not driven by the Plas/tet promoter or the expression of LuxR or LacI is not driven by the Plux/lac promoter). In some embodiments, the expression of LacI, LuxI, and/or LasR is driven by the Plas/tet promoter. In some embodiments, the expression of LuxR, LasI, and/or TetR is driven by the Plux/lac promoter. In a particular embodiment, Plas/tet drives LasR, LuxI and LacI expression, representing the node X in FIG. 1B, whereas Plux/lac regulates transcription of LuxR, LasI, and TetR, representing the node Y.

In some aspects, the disclosure relates to a synthetic gene circuit for modeling complex patterns comprising a first plasmid or node and a second plasmid or node with each plasmid or node comprising two hybrid promoters. The first plasmid or node comprises a first hybrid promoter, wherein the first hybrid promoter is activated by a first gene and inhibited by a second gene; a second hybrid promoter, wherein the second hybrid promoter is activated by a third gene and inhibited by a fourth gene; a first reporter gene, wherein the second hybrid promoter drives the expression of the first reporter gene; and a first combination of genes. The second plasmid or node comprises a third hybrid promoter, wherein the third hybrid promoter is activated by the first gene and inhibited by the second gene; a fourth hybrid promoter, wherein the fourth hybrid promoter is activated by the third gene and inhibited by the fourth gene; a second reporter gene, wherein the third hybrid promoter drives the expression of the second reporter gene; and a second combination of genes. The first hybrid promoter and the third hybrid promoter are the same hybrid promoter, while the second hybrid promoter and the fourth hybrid promoter are the same hybrid promoters. The reporter genes and the autoinducer synthase genes in the two plasmids are different.

In some aspects, the first combination of genes comprises the first gene, the fourth gene, and a first autoinducer synthase gene while the second combination of genes comprises the second gene, the third gene, and a second autoinducer synthase gene. The product of the first autoinducer synthase gene forms a complex with the product of the first gene to activate the first hybrid promoter and the third hybrid promoter. The product of the second autoinducer synthase gene forms a complex with the product of the third gene to activate the second hybrid promoter and the fourth hybrid promoter.

The partial differential equation (PDE) model simulations and experimental measurements strongly support that the observed ring patterns from MINPAC are driven by a RD-based oscillatory gene network with propagating wavefront, the so-called clock and wavefront mechanism. It is noteworthy that a single PDE model could be used to recapitulate and predict all the MINPAC-directed biological patterns. Furthermore, the close connections between gene network topology (circuit architecture) and its induced spatial pattern formation were verified.

Figure 1C:
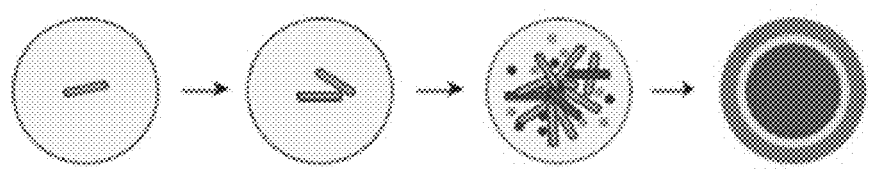
Figure 1D:
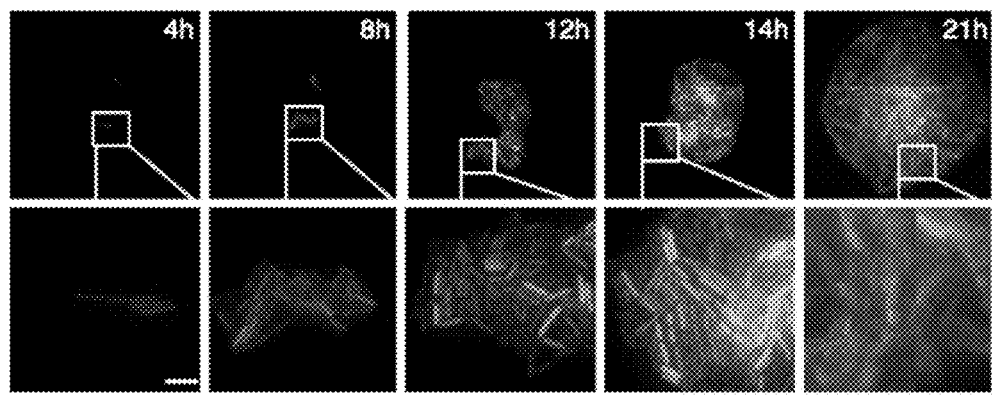

Transformation of MINPAC into *E. coli* cells showed that the synthetic gene circuit could direct single cells to self-organize into spatial patterns. As shown in FIG. 1C, the *E. coli* cell cultures were serially diluted single cells before seeding on a semi-solid minimal M9 medium. Live single cell time-lapse fluorescence microscopy showed the early stage of pattern formation (FIG. 1D). After an initial phase of uniform fluorescence (4 & 8 hours), the cells differentiated into equivalent numbers of green and red fluorescence in a disordered, seemingly random spatial distribution (12 & 14 hours). As microcolonies grew to ~100 μm in diameter (between 14 and 21 hours of growth), a red-center green out-circle fluorescence pattern starts to emerge (FIG. 1D). These results illustrate that the engineered pattern formation is scale-dependent at the early stage, and the pattern starts to emerge only after cell number reaches a certain threshold. While outcomes of cell-cell variability are hard to predict initially or at microscopic scale, as the stochastic growth progresses through time, the population starts to synchronize and converge to a collective behavior and become more predictable as time progress or at macroscopic scale.

To further investigate the circuit's capability in directing pattern formation at macroscopic scale, a long-term experiment was performed by culturing single cell-initiated colonies on agar plates for up to 96 hours. Time-lapse colony imaging results showed that the single colony had no obvious pattern at 15 hr and exhibited a weak yellow flat disk, which suggest that the cells expressing either GFP or mCherry were distributed without order (FIG. 6). This is consistent with the microscopic observations. After 24 hr, cells in the colony started to differentially and orderly express GFP and mCherry, and they self-organized into a stable double-ring pattern of an outer GFP-ring and inner mCherry disk at 48 hr (FIGS. 1E and 6), with a small temporary yellow ring between these two rings (FIG. 6). The double-ring pattern was stable with time. Fluorescence quantification also confirms higher GFP expression for cells on the edge of the colony and higher mCherry expression for cells in the center (FIG. 1F).

To rule out the possibility that circuit-independent factors such as nutrition or growth are responsible for the pattern, two control circuits, one with GFP and mCherry expressed from constitutive promoters and one with GFP and mCherry expressed from hybrid promoters Plas/tet and Plux/lac were tested. No obvious ring patterns were observed at 24 or 48 hrs (FIGS. 7A and 7B). Therefore, the MINPAC circuit is responsible for the self-organized ring pattern in the single colonies.

To garner a quantitative and mechanistic understanding of the ring patterning process, a PDE model was built to mathematically describe the production, regulation, transport, and diffusion of autoinducers C6 and C12. LuxI and LasI's expression in MINPAC governs the synthesis of C6 and C12, which can diffuse out of and back into cells to further regulate the intrinsic transcriptional network MINPAC and determine cells' fate spatially. Thus, the extracellular C6 and C12 kinetics serve as a predictive snapshot of the spatial pattern and could represent the differential expression of mCherry and GFP, respectively (see Examples for more details). Fitted with biologically feasible parameters, our model shows the two autoinducers harbor similar dynamics to experimental fluorescence intensities across the colony and can reproduce experimentally observed ring pattern in two-dimensional geometry (FIG. 1G). Such corroboration between the RD-based PDE model and experimental results further verified that observed ring pattern was the result of MINPAC regulated RD process.

Figure 2A:
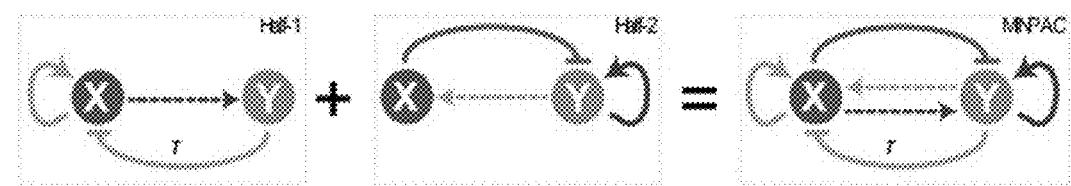
FIGS. 2A-2G show, in accordance with certain embodiments, MINPAC directs ring pattern formation through a reaction-diffusion based clock and wavefront mechanism.
Figure 2B:
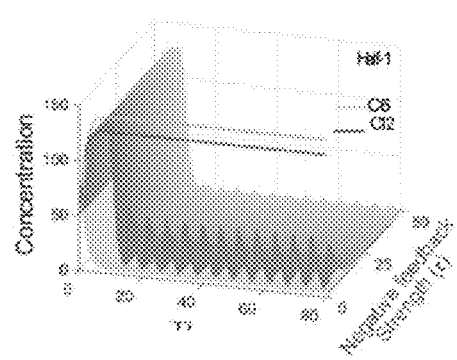
Figure 2C:
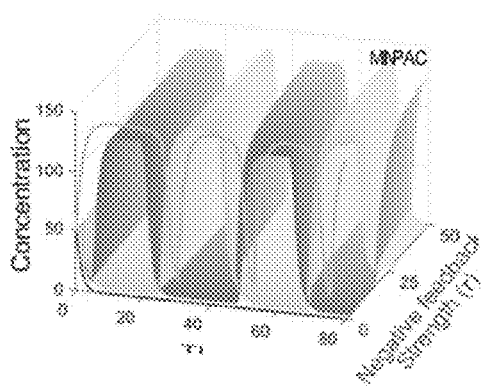
Figure 8A:
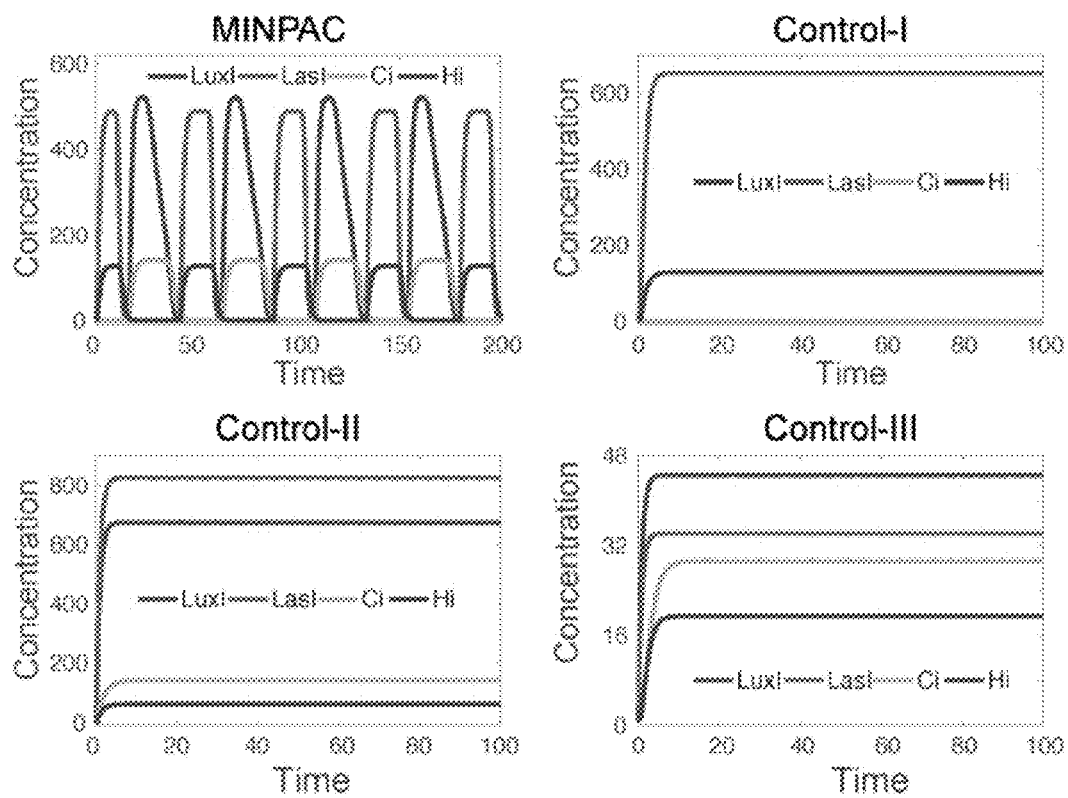
FIG. 8A depicts, in accordance with certain embodiments, dynamic comparison between MINPAC and the three control circuits when diffusion rate is 0. The top left image is a time series simulation of the MINPAC system, which show a stable periodic oscillation for LuxI, LasI, $C_i$, and $H_i$. However, the Control circuits go to stable steady states. Multiple parameter values were tested and similar results are produced.
Figure 9A:
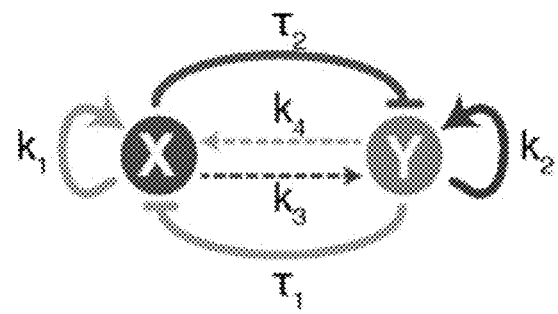
FIGS. 9A-9E show, in accordance with certain embodiments, that MINPAC harbors a great robustness and amplitude against parameter changes to generate temporal oscillation.
Figure 9B:
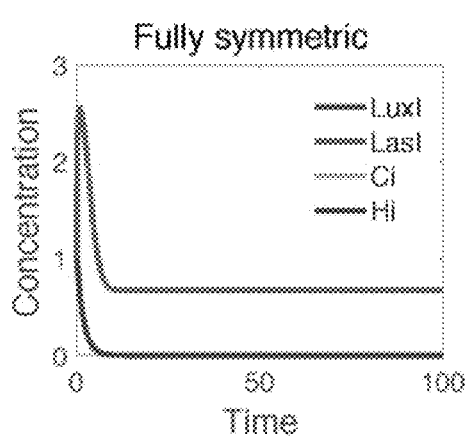
Figure 9C:
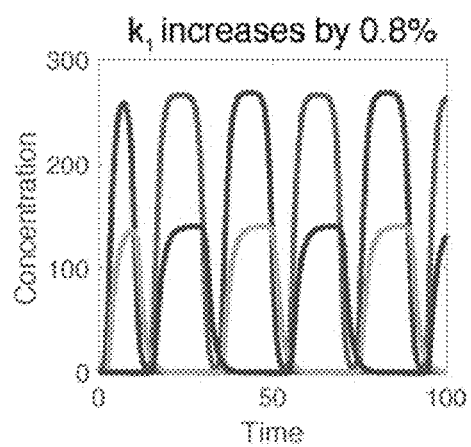
Figure 9D:
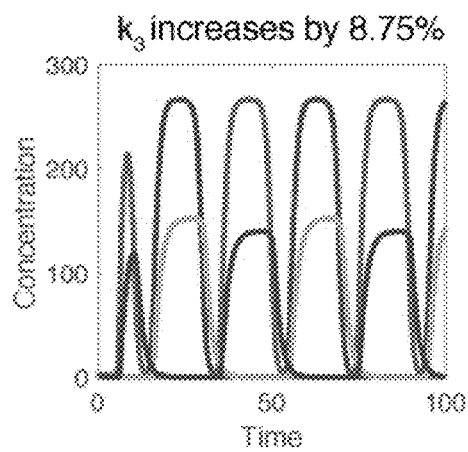
Figure 9E:
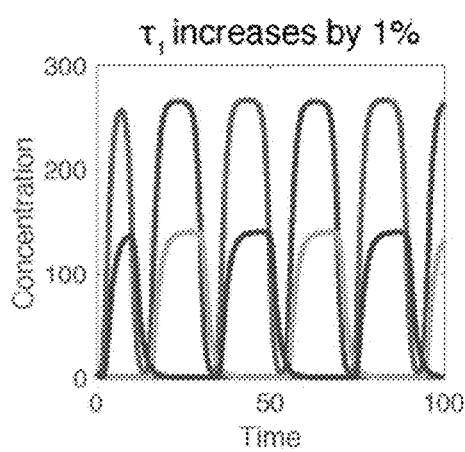

To further investigate how MINPAC directs the generation of ring pattern, deterministic analysis for the reaction term of the RD model (for example, the ODE part) was performed. Time series showed that MINPAC has an oscillating reaction part (FIG. 8A), suggesting the temporal oscillation could drive an organized pattern formation across the expanding colony. From a network topology point of view, MINPAC has two topologically equivalent motifs where a self-activating node activates the other node and it in turn inhibits the self-activating node (FIG. 2A), each forming a robust positive-plus-negative oscillator topology. A fully symmetric MINPAC topology would rapidly go to stable steady states without oscillation, but little asymmetry between the two motifs would lead to a robust oscillation (FIGS. 9C-9E). The model-comparison results showed that oscillation from one-motif topology is highly dependent on the strength of its negative feedback ($\tau$), which is vital for cyclic gene expression (FIG. 2B). However, the two-motif MINPAC harbors a greater robustness and amplitude against parameter perturbations to generate temporal oscillation (FIG. 2C). Such robustness enhances the likelihood of observing the desired phenotypic outputs from the synthetic gene circuit.

In the MINPAC circuit, promoter functionality tests show LacI is less efficient to inhibit promoter Plux/lac (FIG. 5A) compared to tetR to Plas/tet (FIG. 5B), supporting that the asymmetric MINPAC could maintain an oscillatory gene expression profile as the molecular clock. Moreover, the autoinducers' physical diffusion on the agar medium and colony outward expansion (represented as one diffusion term in the PDE model) constitute the propagating wavefront. Finally, the integration of clock and wavefront gates the engineered bacterial cells into subgroups and segment spatially, generating periodic structures. This reaction-diffusion based pattern formation is widely used to explain somitogenesis in development.

Figure 2D:
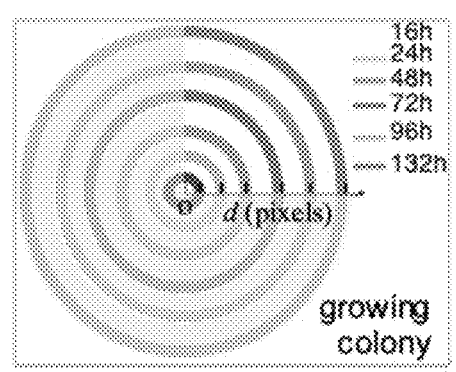
Figure 2E:
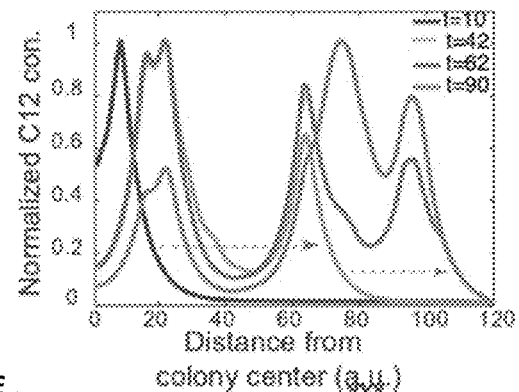
Figure 8B:
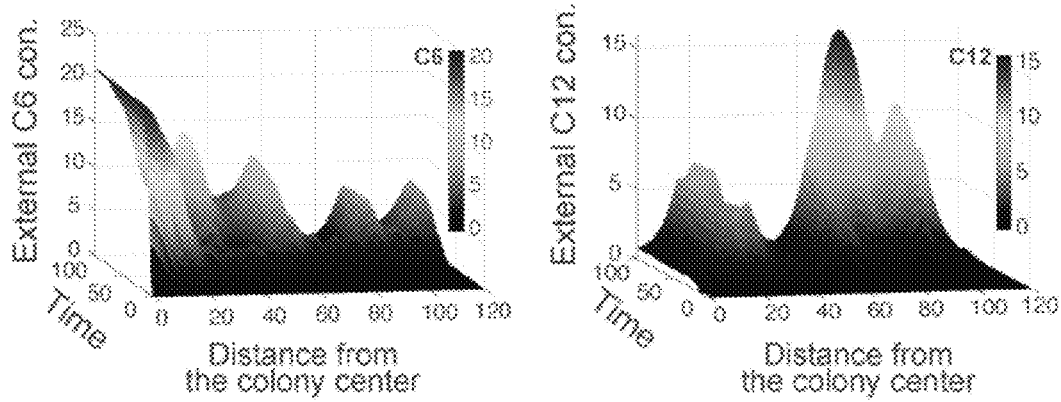
FIG. 8B depicts, in accordance with certain embodiments, a model simulation for external C6 and C12 dynamics with time and space from the MINPAC reaction-diffusion model. Simulations start from the center of a colony.

One interesting phenomenon among vertebrate species is the variations of somite numbers, which is determined by the axis growth and presomitic mesoderm lifetime during embryogenesis. Analogously, multiple or even indefinite number of stripes for a continuously growing colony would be expected (illustrated in FIG. 2D), and colonies with different sizes would have different number of stripes when the oscillation frequency and colony expanding rates were constant across colonies. The PDE model simulated the temporal dynamics of C12 on the spatial scale and new peaks emerged periodically at the wavefront (FIGS. 2E and 8B). Experimentally, ring patterns with multiple stripes were also observed sequentially by time lapse imaging of large colonies (FIGS. 2F-G), as modeling predicted. Collectively, these results suggest that the ring patterns observed are the outcomes of the spatiotemporal interaction of oscillatory dynamics owing to the network topology and the movement stemming from the diffusion process.

Figure 2F:
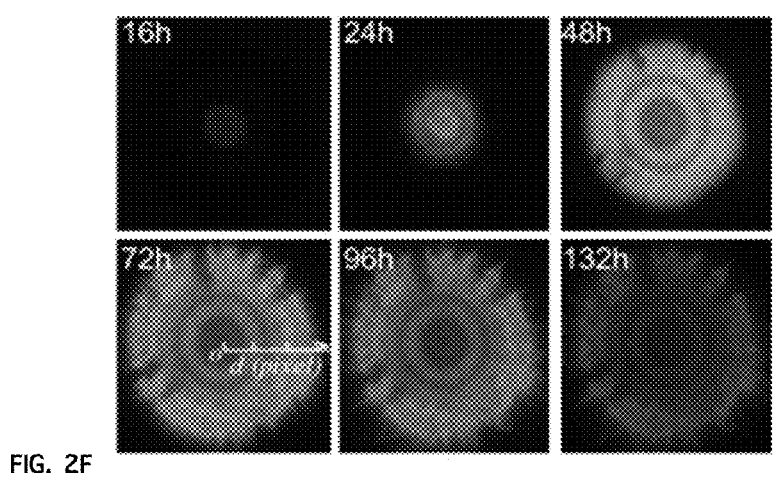

However, even a macroscopic RD system could still be highly sensitive to initial conditions due to the nonlinearity of the network interactions, evidenced by diverse patterns shown in FIG. 3A, some colonies self-organize into a reversed double-ring pattern with GFP accumulating in the inner ring and mCherry on the outer ring (top). A more complicated pattern was also observed, in which two GFP rings alternating with two mCherry rings, forming a multiple GFP-mCherry ring pattern (FIG. 2F and FIG. 3A, bottom). Given that these different patterns emerge from the same MINPAC circuit operating in the same cells and under the same conditions, the patterns were likely due to random variations of the initial concentrations of intracellular proteins and autoinducers. This was confirmed with computation tests.

The computational model tested the various initial conditions of the PDE but kept all the parameters the same. The model indeed reproduces the experimental patterns (FIG. 3B). Furthermore, these differences of the patterns suggest the system was not at steady state and, instead, was evolving towards the steady state. The initial condition determined the starting point of the MINPAC system, which will go through a temporal "non-oscillating" spiral (blue line in FIG. 3C) and finally approach oscillation periods (starting from red curve in FIG. 3C). Quantitative simulations show that the oscillatory system, with different initial points, could require significantly different times, so called Poincare return time, to approach the first stable limit cycle (FIG. 3D). Thus, the initial condition and resulting approach-time variances led to diverse patterns with different stripes (besides colony size). These results illustrated that initial conditions play an important role in shaping the formation of biological patterns, which is consistent with recent theoretical analysis. Accordingly, methods of detecting the pattern formation of a synthetic gene circuit are described. In a specific embodiment, the method comprises defining a PDE model based on a reaction-diffusion process within the synthetic gene circuit; defining a set of boundary conditions and a set of initial conditions for the reaction-diffusion model based upon at least one topology of the synthetic gene circuit, a plurality of biologically feasible coefficient values, and an external perturbation; and determining a pattern expression dynamic for the synthetic gene circuit by numerically solving the PDE model. The PDE model comprising a plurality of equations each modeling a biochemical reaction within the synthetic gene circuit, gene activation and gene repression being represented as hill functions, wherein the equations each comprise a plurality of coefficients each representing one of promoter basal expression, feedback, protein production, protein degradation, activation rate, and repression rate. For example, the PDE model can comprise the equation 7-12 set forth in the examples.

Figure 10A:
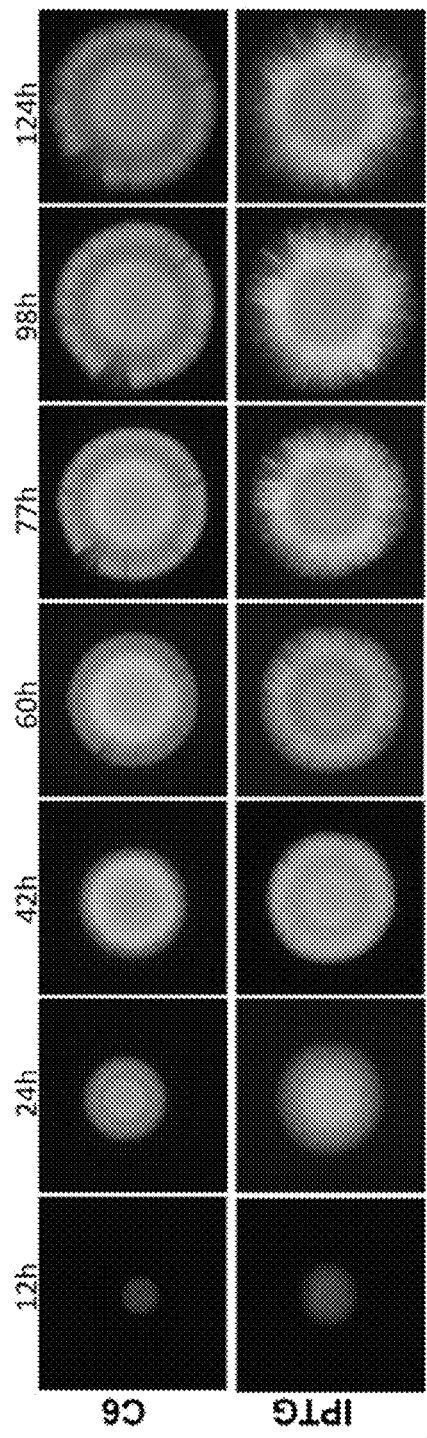
FIGS. 10A-10C show, in accordance with certain embodiments, the tunability of the pattern formation from MINPAC using external inducers.
Figure 10B:
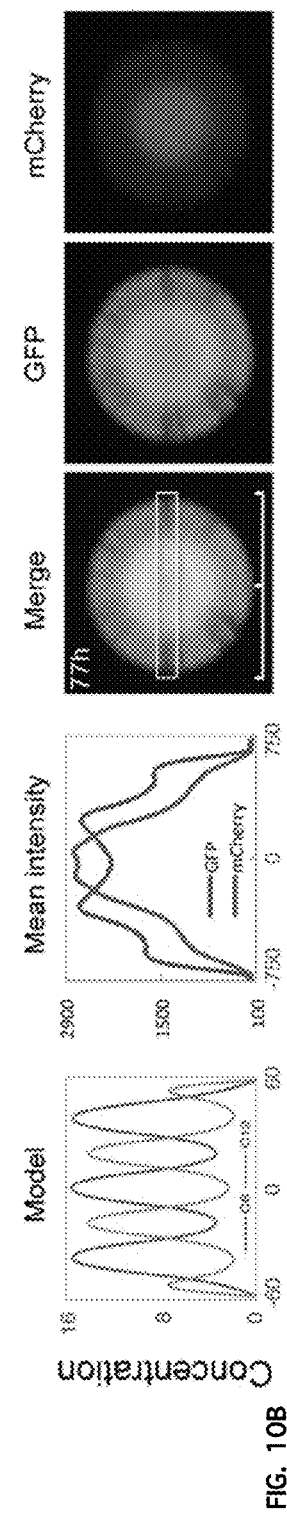

To further examine the pattern's controllability, external inducers to perturb the regulations of MINPAC and hence pattern formation were applied. C6, when applied externally, would promote GFP expression and also LasI and TetR production, which could both activate and inhibit mCherry expression. So the net impact of C6 induction was nonlinear and nontrivial. Using the PDE model to simulate C6 application, it was predicted that a multiple GFP-mCherry ring pattern would appear when MINPAC is induced with external C6 (FIG. 4A, top). Experimentally, the medium was supplemented with $1\times10^{-8}$ M C6, the colony was grown following the same protocol. Results showed that the colony first formed an outer GFP ring and a reddish yellow core at 24 hr, which became a red core at 60 hr (FIG. 10A). Strikingly, two GFP rings emerged at 77 hr whereas mCherry mostly accumulated in the center (FIG. 4B, top, and FIG. 10A). Quantified fluorescence intensities also illustrated that there were four peaks for GFP and one significant peak for mCherry, which is in line with model predictions (FIG. 4B). The inconsistent dynamics between predicted C6 concentrations and measured mCherry intensities was probably because of the slow degradation rate of mCherry protein in living cells. Similarly, external C12 induction resulted in two GFP rings with unbalanced intensities (FIG. 10B).

Figure 10C:
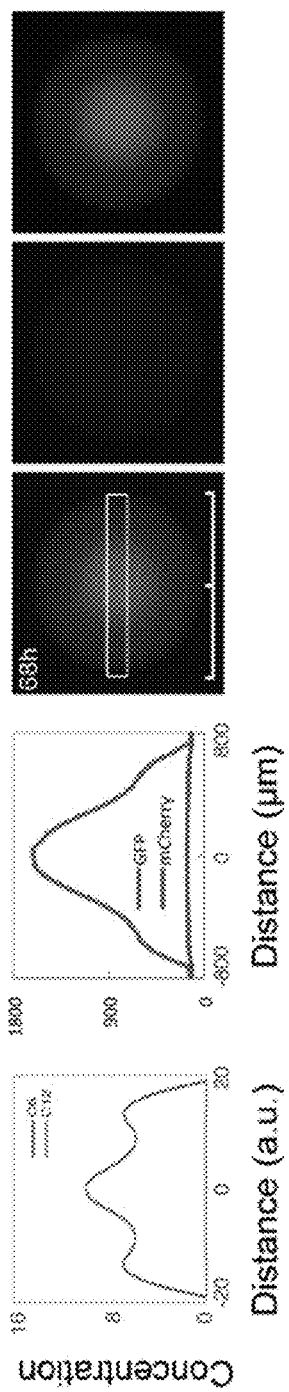

IPTG and aTc induction, on the other hand, could modulate the strength of mutual inhibition in the circuit. IPTG counteracts LacI's inhibition on Plux/lac, which leads to more LasI expression and intracellular C12 production. Simulating these changes by perturbing corresponding parameters, the model predicted a target-like mCherry ring with an outer GFP ring pattern (FIG. 4A, bottom), which was further verified by experimental data (FIG. 4B, bottom). Time course showed that cells in the inner side of the GFP ring started to express mCherry, showing as a yellow ring, at ~60 hr and was stable until the 124th hour (FIG. 10A). Inducer aTc's impacts were similarly predicted and experimentally confirmed (FIG. 10C). Taken together, these results illustrated the controllability of the MINPAC circuit and its directed patterns formation. It is noteworthy that these patterns generated in single colonies autonomously without any predefined spatial cues and the regular structures are robust and stable once formed.

Because the synthetic circuit directed cell-cell communication is established as a viable strategy to generate RD-based and tunable patterns, this method is usable for studying the fundamental question of relationship between gene network topology and resulting multicellular pattern.

In one implementation, a perturbed MINPAC topology was designed, where the intercellular X-Y communication modules were replaced by intercellular auto-activations of X and Y (FIG. 4C, top, specific experimental design can be found in FIG. 11A). Although there was still autoinducer diffusion, the perturbed circuit mitigated the interactions and dependency between X and Y and would remarkably change the intrinsic dynamics. Both experimental observation and model simulation showed no specific pattern but a reddish colony (FIG. 4C, top row). The perturbed MINPAC topology was further altered by removing the mutual inhibition module to construct a circuit with two positive feedback motifs (FIG. 4C, middle row) reinforced by intercellular activations. A yellow fluorescent colony with strong GFP and mCherry expression was observed, which was consistent with the model analysis. Lastly, a sub-network of MINPAC was engineered where the mutual inhibition was removed but the other regulatory edges were kept (FIG. 4C, bottom row). Interestingly, this mutual-activation topology resulted in a weak yellow target-like ring pattern with low GFP and mCherry expression (FIG. 4C, bottom row). Previous theoretical studies demonstrated that mutual-activation circuit with autoregulation is multistable and harbors a big parameter space for low-low state. The model analysis also confirmed the low-GFP and low-mCherry expression in this sub-network (FIG. 4C, bottom row). Taken together, each control circuit with different topology has different fluorescence patterns, but none of them show the alternating ring patterns, which indicated that the multiple-ring pattern is unique to MINPAC circuit.

Biological pattern formation requires complex gene regulation networks and accurate cell-cell coordination. Indeed, coordinated cell population behavior in response to self-regulated morphogen kinetics is a common phenomenon in development. Also described herein are methods for generating an expression pattern, for example, a ring pattern, a complex ring pattern like a target, or a striped pattern of at least one gene. Once the synthetic gene circuit is introduced into a cell, the expression pattern of at least one of the reporter genes in the synthetic gene circuit is in a ring pattern or a striped pattern. Accordingly, the disclosure relates to a method of generating an expression pattern of a first reporter gene comprising introducing into a cell a synthetic gene circuit and providing to the altered cell a first inducer compound, wherein the first inducer compound induces hybrid promoter that drives the expression of the first reporter gene. The cell may be a prokaryotic cell, like an $E.$ $coli$, or may be a eukaryotic cell. In some implementations, the complexity of the pattern is modulated by providing to the altered cell a compound that alters the strength of the mutual modulation in the synthetic gene circuit, which may, for example, result in the formation of a striped ring pattern, such as a target pattern.

The synthetic gene circuit introduced into the cell comprises two nodes or plasmids. The first plasmid comprises a first hybrid promoter, wherein the first hybrid promoter is activated by a first gene and inhibited by a second gene; a second hybrid promoter, wherein the second hybrid promoter is activated by a third gene and inhibited by a fourth gene; the first reporter gene, wherein the second hybrid promoter drives the expression of the first reporter gene; and a first combination of genes comprising the first gene, the fourth gene, and a first autoinducer synthase gene. The second plasmid comprises a third hybrid promoter, wherein the third hybrid promoter is activated by the first gene and inhibited by the second gene; a fourth hybrid promoter, wherein the fourth hybrid promoter is activated by the third gene and inhibited by the fourth gene; a second reporter gene, wherein the third hybrid promoter drives the expression of the second reporter gene; and a second combination of genes comprising the second gene, the third gene, and a second autoinducer synthase gene. The product of the first autoinducer synthase gene forms a complex with the product of the first gene to activate the first hybrid promoter and the third hybrid promoter, while the product of the second autoinducer synthase gene forms a complex with the product of the third gene to activate the second hybrid promoter and the fourth hybrid promote. In the synthetic gene circuit, the first hybrid promoter and the third hybrid promoter are the same hybrid promoters, while the second hybrid promoter and the fourth hybrid promoter are the same hybrid promoters. On the other hand, the first reporter gene and the second reporter gene are different, while the first autoinducer synthase gene and the second autoinducer synthase gene are also different.

In a particular embodiment, the first plasmid comprises a first Plas/tet promoter; a first Plux/lac promoter; the first reporter gene; and the first combination of genes comprises LacI, LuxI, and LasR, while the second plasmid comprises a second Plas/tet promoter; a second Plux/lac promoter; the second reporter gene; and the second combination of genes comprises LuxR, LasI, and TetR. The first Plas/tet promoter drive the expression of the first reporter gene and the second Plux/lac promoter drive expression of the first combination of genes, while the second Plux/lac promoter drive the expression of the second reporter gene and the second Plas/tet promoter drive expression of the second combination of genes. Accordingly, in some implementations, the first inducer compound is C6 and the amount of the first inducer compound provided is $1 \times 10^{-8}$ M, the altered cell is cultured in the presence of the first inducer compound for at least 70 hours, for example at least 77 hours. To produce a striped or target-like expression pattern, the method further comprises providing IPTG to the altered cell. In a certain implementation, the concentration of IPTG is 10 μM and the altered cell is cultured in the presence of IPTG for at least 70 hours, for example at least 77 hours.

Also described herein is a method of detecting the expression pattern formation of a synthetic gene circuit. The method comprises defining a PDE model based on a reaction-diffusion process within the synthetic gene circuit. The PDE model comprises a plurality of equations each modeling a biochemical reaction within the synthetic gene circuit, gene activation and gene repression being represented as hill functions, wherein the equations each comprise a plurality of coefficients each representing one of promoter basal expression, feedback, protein production, protein degradation, activation rate, and repression rate. The method further comprises defining a set of boundary conditions and a set of initial conditions for the reaction-diffusion model based upon at least one topology of the synthetic gene circuit, a plurality of biologically feasible coefficient values, and an external perturbation and determining a pattern expression dynamic for the synthetic gene circuit by numerically solving the PDE model.

In certain implementations, the method detects the expression pattern formation of a synthetic gene circuit described herein. For example, the synthetic gene circuit comprises a first plasmid (which comprises a first hybrid promoter, a second hybrid promoter, a first reporter gene, and a first combination of genes) and a second plasmid (which comprises a third hybrid promoter, a fourth hybrid promoter, a second reporter gene, and a second combination of genes). The first hybrid promoter is activated by a first gene and inhibited by a second gene. The second hybrid promoter is activated by a third gene, inhibited by a fourth gene, drives the expression of the first reporter gene. The first combination of genes comprising the first gene, the fourth gene, and a first autoinducer synthase gene. The third hybrid promoter is activated by the first gene and inhibited by the second gene. The fourth hybrid promoter is activated by the third gene and inhibited by the fourth gene. The third hybrid promoter drives the expression of the second reporter gene. The second combination of genes comprises the second gene, the third gene, and a second autoinducer synthase gene. In the pattern-forming synthetic gene system, the first hybrid promoter and the third hybrid promoter are the same hybrid promoters, while the second hybrid promoter and the fourth hybrid promoter are the same hybrid promoters. However, the first reporter gene and the second reporter gene are different, and the first autoinducer synthase gene and the second autoinducer synthase gene are different. The product of the first autoinducer synthase gene forms a complex with the product of the first gene to activate the third hybrid promoter and the third hybrid promoter, and the product of the second autoinducer synthase gene forms a complex with the product of the third gene to activate the second hybrid promoter and the fourth hybrid promoter.

In some implementations, the PDE model is defined as follows in Equations 7-12.

$$\frac{\partial U}{\partial t} = \beta_1 + \frac{k_1 \cdot (U \cdot H_i)^{n1}}{1 + (U \cdot H_i)^{n1}} \cdot \frac{1}{1 + A^{m1}} - d_1 \cdot U \quad \text{(Eq 7)}$$

-continued $$\frac{\partial A}{\partial t} = \beta_2 + \frac{k_2 \cdot (A \cdot C_i)^{n2}}{1 + (A \cdot C_i)^{n2}} \cdot \frac{1}{1 + U^{m2}} - d_2 \cdot A \quad \text{(Eq 8)}$$

$$\frac{\partial C_i}{\partial t} = \frac{k_2 \cdot U^{n3}}{K_c^{n2} + U^{n3}} - d_3 \cdot C_i + D_c \cdot (C_e - C_i) \quad \text{(Eq 9)}$$

$$\frac{\partial H_i}{\partial t} = \frac{k_4 \cdot A^{n4}}{k_h^{n4} + A^{n4}} - d_4 \cdot H_i + D_h \cdot (H_e - H_i) \quad \text{(Eq 10)}$$

$$\frac{\partial C_e}{\partial t} = -D_c \cdot (C_e - C_i) - d_5 \cdot C_e + D_1 \cdot \frac{\partial^2 C_e}{\partial x^2} \quad \text{(Eq 11)}$$

$$\frac{\partial H_e}{\partial t} = -D_h \cdot (H_e - H_i) - d_6 \cdot H_e + D_2 \cdot \frac{\partial^2 H_e}{\partial x^2} \quad \text{(Eq 12)}$$

U is the expression of the first autoinducer synthase gene. A is the expression of the second autoinducer synthase gene. $\beta_1$ and $\beta_2$ are the basal expressions from the first hybrid promoter and the second hybrid promoter. $n_1$ and $n_2$ are hill coefficients for activation of the promoters from protein complex with the first autoinducer synthase gene or the second autoinducer synthase gene. $m_1$ and $m_2$ are hill coefficients for repression of the promoters from protein complex with the first autoinducer synthase gene or the second autoinducer synthase gene. $C_i$ is the intracellular concentration of an inducer of the first autoinducer synthase gene. $H_i$ is the intracellular concentration of an inducer of the second autoinducer synthase gene. $k_3$ and $k_4$ are the production rates of the inducer of the first autoinducer synthase gene and the inducer of the second autoinducer synthase gene. $K_c$ and $K_h$ are the half maximal effective concentrations for production of the inducer of the first autoinducer synthase gene and the inducer of the second autoinducer synthase gene. $d_7$ and $d_8$ are the rates of internal degradation of the inducer of the first autoinducer synthase gene and the inducer of the second autoinducer synthase gene. a $D_c$ and $D_h$ are the diffusion rates of the inducer of the first autoinducer synthase gene and the inducer of the second autoinducer synthase gene through a cellular membrane $d_5$ and $d_6$ are degradation rates of external $C_6$ and $C_{12}$, and $D_1$ and $D_2$ are the diffusion constants for external $C_6$ and C across the colony on the medium. $C_e$ is the extracellular concentration of an inducer of the first autoinducer synthase gene. $H_e$ is the extracellular concentration of an inducer of the second autoinducer synthase gene.

Illustrative, Non-Limiting Examples in Accordance with Certain Embodiments

The disclosure is further illustrated by the following examples that should not be construed as limiting. The contents of all references, patents, and published patent applications cited throughout this application, as well as the Figures, are incorporated herein by reference in their entirety for all purposes.

1. Materials and Methods a. Strains, Media and Chemicals

All cloning experiments were performed in *Escherichia coli* DH10B (Invitrogen). MINPAC was transformed into *E. coli* K-12 MG1655 strain with lacI-/- (1) to grow pattern. Cells during cloning were cultured in liquid or solid Luria-Bertani (LB) broth medium with 100 μg/mL ampicillin at 37° C. Pattern grown on minimal salt medium (M9) supplemented with 100 μg/mL ampicillin and 0.45% glucose at 37° C. Chemicals N-(β-Ketocaproyl)-Lhomoserinelactone (C6, Sigma-Aldrich), isopropyl β-D-1-thiogalactopyranoside (IPTG, Sigma-Aldrich), and anhydrotetracycline (aTc, Sigma-Aldrich) were dissolved in ddH$_2$O and diluted into indicated working concentrations. N-(3-Oxododecanoyl)-L-homoserine lactone (C12, Sigma-Aldrich) was dissolved in dimethyl sulfoxide (DMSO, Sigma-Aldrich) to avoid precipitation. Liquid cultures were shaken in 15 mL tubes at 220 rotations per minute (rpm).

b. Plasmid Construction

Plasmids were constructed using standard molecular biology techniques and all genetic circuits were assembled based on standardized BioBrick methods. Detailed description can be found in reference (2). During molecular cloning, both fragment and vector were separated on 1% TAE agarose gel electrophoresis and purified using PureLink gel extraction Kit (Invitrogen). Purified fragment and vector were then ligated by T4 DNA ligase (New England Biolabs, NEB). The ligation products were further transformed into *E. coli* DH10B and plated on LB agar plate with 100 μg/mL ampicillin for screening. Finally, plasmids extracted by GenElute HP MiniPrep Kit (Sigma-Aldrich) were further confirmed through gel electrophoresis (digested with EcoRI and PstI) and DNA Sequencing (Biodesign sequencing Lab, ASU). All the biological parts used in the paper are obtained from iGEM Registry (http://parts.igem.org/Main_Page) and listed in Table 1. Promoters and each bio-parts were tested before assembly of MINPAC (FIGS. 5A and 5B).

c. Experimental Set-Up for Pattern Growing and Microscopy

One microliter overnight cultured *E. coli* cells harboring MINPAC were serially diluted with M9 medium without antibiotic to 5×10$^5$–5×10$^6$ fold and 5 microliter dilution were then evenly plated on the 10 mL semi-solid M9 minimal medium supplemented with 1 mM MgSO$_4$, 100 μM CaCl$_2$), 100 μg/mL ampicillin, 0.01% g/mL amino acid mixtures and 0.45% glucose on a 5-cm petri dish. Fresh M9 solid medium are made for patterning experiment each time. The concentration of amino acid mixture should be kept around 0.01% g/mL, though the real concentration may range between 0.005%-0.02% g/mL. For optimal patterning and imaging convenience, colorless agarose at 0.4% g/ml was used instead of agar (yellow) to solidify the medium and decrease the influence of the background color on microscopic results. After serial dilutions, the cell concentration is ~1 cell (colony) per microliter according to our experience. And the colony size is negatively correlated with the number of the total colonies in the plate, each plate has 0 to 10 separate colonies in our settings. Petri dishes were covered with parafilm (Pentair, US) to decrease the drying process of the medium and grown in 37° C. incubator. To make the colonies grow larger, petri dishes were placed in a small cabinet with external water to increase the air humidity. For the induction experiments, the inducers (C6, C12, and aTc, and IPTG) was added to the LB medium (~37° C.) before plating into the petri dishes.

Images were taken at indicated times using Nikon Eclipse Ti inverted microscope (Nikon, Japan) at 2× magnification. For continuous observation, the relative position of each colony in the petri dish was labeled and recorded. Exposure time are kept the same during the time course experiments, however, appropriate adjustments are made at some instances especially for the first time point's (12~16 hour) result because of little fluorescent protein expression before 16 hr. The exposure time from fluorescence intensities was normalized to analyze the time course results in FIG. 2F. Brightness and contrast were slightly tuned for presentation of images in the research, however, the mean fluorescence intensities shown in these figures (white boxes on the fluorescence images) were directly acquired from the original images and averaged their intensity values for all the pixels in the white box under the same directions of x-axis (a line goes through the center of the colony). GFP was visualized with an excitation at 472 nm and emission at 520/35 nm and mCherry was visualized with excitation at 562 nm and emission at 641/75 nm using Semrock bandpass filters. For each patterning experiment, ~6 individual colonies were captured and repeated at least two times on different days.

d. Flow Cytometry Measurements

Flow cytometry measurements were performed using Accuri C6 flow cytometer (Becton Dickinson) and all samples were analyzed at 12-hour and 24-hour time points with 488 nm excitation and 530±15 nm emission detection for GFP, and 610 LP for mCherry. For the test of promoter Plux/lac, the 12 hrs data were plotted, and for Plas/tet, the 24 hrs data were plotted. 20,000 individual cells were analyzed for each sample at a slow flow rate. Experiments were repeated two times with three replicates. Data files were further analyzed by MATLAB (MathWorks).

e. Time-Lapse Fluorescence Microscopy

E. coli K-12 MG1655 strain containing MINPAC was inoculated from frozen stock into growth medium (M9 minimal medium supplemented with 0.1% amino acid, 0.45% glucose and 100 µg/mL Ampicillin). The cells were grown for 12 hrs with aeration (300 rpm) at 37° C. To capture colony formation from a single cell, 2% low melting point agarose pad containing 50 µg/mL Ampicillin were prepared according to Young et al. (J. W. Young et al., "Measuring single-cell gene expression dynamics in bacteria using fluorescence time-lapse microscopy." Nat. Protoc. 2011, 7: 80-88). 2 µL diluted overnight culture was put onto agarose pads and slides were incubated at 37° C. in dark. Microscopic images were acquired at different time points using Zeiss Axio inverted fluorescence microscope at 63× magnification (Plan-Apochromat 63×/1.4 DIC), with a Zeiss axiocam 503 mono camera. Images covering approximately 1100 µm×800 µm area were collected and processed by Zeiss Zen2 software.

2. Mathematical Modeling a. Model Construction

In a particular embodiment, the MINPAC circuit is composed of two hybrid promoters (Plux/lac and Plas/tet), two activators (LuxR and LasR), two repressors (LacI and TetR), two AHL autoinducer synthases (LuxI and LasI), and two promoter reporters (GFP and mCherry). LasI and LuxI are two synthases responsible for the synthesis of autoinducer 3-oxo-C12-HSL (C12) and 3-oxo-C6-HSL (C6), respectively. The two small autoinducers (morphogens) can diffuse out of and back into cells to mediate cell-cell communication and coordinate population behaviors on a spatial domain. Plux/lac activity is determined by the relative concentrations of LacI and LuxR-C6, which is a complex of LuxR protein and intracellular C6 ($C_i$). Similarly, Plas/tet dynamics is determined by the relative concentrations of TetR and LasR-C12, which is a complex of LasR protein and intracellular C12 ($H_i$).

To develop a quantitative and mechanistic understanding of the MINPAC-directed ring patterning process, a partial differential equation (PDE) model was developed based on the reaction-diffusion process involving the regulation, production, and diffusion of morphogens C6 and C12. For simplicity, only one equation was used to overall describe the DNA transcription and protein translation processes, instead of separately describing them. Both the activation and repression are described as hill functions. The ordinary differential equations for LasR (S), LacI (C), LuxI (U), LuxR (X), TetR (E), and LasI (A) were derived from the biochemical reactions depicted in FIG. 1A:

$$\frac{\partial S}{\partial t} = \beta_1 + \frac{k_{11} \cdot (S \cdot H_i)^{n1}}{1+(S \cdot H_i)^{n1}} \cdot \frac{1}{1+E^{m1}} - d_{11} \cdot S \quad (Eq\ 1)$$

$$\frac{\partial C}{\partial t} = \beta_1 + \frac{k_{12} \cdot (S \cdot H_i)^{n1}}{1+(S \cdot H_i)^{n1}} \cdot \frac{1}{1+E^{m1}} - d_{12} \cdot C \quad (Eq\ 2)$$

$$\frac{\partial U}{\partial t} = \beta_1 + \frac{k_{13} \cdot (S \cdot H_i)^{n1}}{1+(S \cdot H_i)^{n1}} \cdot \frac{1}{1+E^{m1}} - d_{13} \cdot U \quad (Eq\ 3)$$

$$\frac{\partial X}{\partial t} = \beta_2 + \frac{k_{21} \cdot (X \cdot C_i)^{n2}}{1+(X \cdot C_i)^{n2}} \cdot \frac{1}{1+C^{m2}} - d_{21} \cdot X \quad (Eq\ 4)$$

$$\frac{\partial E}{\partial t} = \beta_2 + \frac{k_{22} \cdot (X \cdot C_i)^{n2}}{1+(X \cdot C_i)^{n2}} \cdot \frac{1}{1+C^{m2}} - d_{22} \cdot E \quad (Eq\ 5)$$

$$\frac{\partial A}{\partial t} = \beta_2 + \frac{k_{23} \cdot (X \cdot C_i)^{n2}}{1+(X \cdot C_i)^{n2}} \cdot \frac{1}{1+C^{m2}} - d_{23} \cdot A \quad (Eq\ 6)$$

where $\beta_1$ and $\beta_2$ are the basal expressions from Plas/tet and Plux/lac, respectively. The middle term in each equation is the positive feedback from LasR-C12 or LuxR-C6 complex and negative feedback from TetR or LacI, respectively. The last term of each equation is the degradation term. $n_1$ and $n_2$, $m_1$ and $m_2$ are the hill coefficients for activation or repression to the promoters from protein complex, like the LuxR-C6 dimer and LacI tetramer. Parameters $k_{ij}$ represent the production rates and $d_{ij}$ represent the degradation rates for proteins LasR, LacI, LuxI, LuxR, TetR, and LasI, respectively.

LasR, LacI, LuxI are produced from the same promoter Plas/tet and have similar production terms. The three proteins were assumed to have similar degradation rates and similar dynamics and use LuxI to represent the LasR and LacI. Similarly, LasI was used to represent LuxR and TetR expression dynamics from Plux/lac. Thus the above six equations could be simplified by the following two equations:

$$\frac{\partial U}{\partial t} = \beta_1 + \frac{k_1 \cdot (U \cdot H_i)^{n1}}{1+(U \cdot H_i)^{n1}} \cdot \frac{1}{1+A^{m1}} - d_1 \cdot U \quad (Eq\ 7)$$

$$\frac{\partial A}{\partial t} = \beta_2 + \frac{k_2 \cdot (A \cdot C_i)^{n2}}{1+(A \cdot C_i)^{n2}} \cdot \frac{1}{1+U^{m2}} - d_2 \cdot A \quad (Eq\ 8)$$

Next, the dynamics of C6 and C12, whose biosynthesis primarily depends on synthases LuxI and LasI, respectively, were considered. Internal C6 and C12 can diffuse out of and into cells, and bacterial cells further respond to the autoinducers when their concentrations exceed a certain threshold. Based on this, the internal C6 ($C_i$) and C12 ($H_i$) dynamics can be described with the following equations:

$$\frac{\partial C_i}{\partial t} = \frac{k_2 \cdot U^{n3}}{K_c^{n2} + U^{n3}} - d_3 \cdot C_i + D_c \cdot (C_e - C_i) \quad (Eq\ 9)$$

$$\frac{\partial H_i}{\partial t} = \frac{k_4 \cdot A^{n4}}{k_h^{n4} + A^{n4}} - d_4 \cdot H_i + D_h \cdot (H_e - H_i) \quad (Eq\ 10)$$

where the first term describes the production of $C_i$ and $H_i$ with the production rate $k_3$ and $k_4$, and $K_e$ and $K_h$ are the half maximal effective concentrations for $C_6$ and $C_{12}$ productions, respectively. Hill coefficients $n_3$ and $n_4$ indicate the nonlinearity for the intracellular synthesis of C6 and C12 from LuxI and LasI, respectively. The middle term is internal degradation of the two molecules with the rate of $d_7$ and $d_8$, and the last term is the diffusion through the cell membrane (molecule transport), with a diffusion rate $D_e$ and $D_h$. $C_e$ and $H_e$ are the external C6 and C12, which diffuse across the cell colony on the M9 agarose medium. Then, the following two equations were used to describe $C_e$ and He dynamics:

$$\frac{\partial C_e}{\partial t} = -D_c \cdot (C_e - C_i) - d_S \cdot C_e + D_1 \cdot \frac{\partial^2 C_e}{\partial x^2} \quad \text{(Eq 11)}$$

$$\frac{\partial H_e}{\partial t} = -D_h \cdot (H_e - H_i) - d_6 \cdot H_e + D_2 \cdot \frac{\partial^2 H_e}{\partial x^2} \quad \text{(Eq 12)}$$

where $d_5$ and $d_6$ are degradation rates of external $C_6$ and $C_{12}$, and $D_1$ and $D_2$ are the diffusion constants for external $C_6$ and C across the colony on the medium, respectively.

It is noteworthy that although Plux/lac activity is activated by the complex of LuxR and intracellular C6, the quorum-sensing mechanism is cell population density-dependent. In other words, Plux/lac can be activated only when the local environmental C6 reaches to a certain threshold. Thus, it is the external C6 and C12 determine the dynamics of MIN-PAC as well as the patterning process. Furthermore, since mCherry and GFP are two reporters of the hybrid promoters Plas/tet and Plux/lac, so external C6 (from LuxI gene, Ce) and C12 (from LasI gene, He) can be used to equivalently simulate mCherry and GFP dynamics.

Taken together, six equations (Eqs 7-12) were derived to model the MINPAC dynamics, including LuxI, LasI, $C_i$, $H_i$, $C_e$, and $H_e$. And the extracellular C6 ($C_e$) and C12 ($H_e$) kinetics can be used as a predictive snapshot of the spatial pattern, and represent the differential expression of mCherry and GFP, respectively. This two-component reaction diffusion equations model was then used to understand MINPAC-directed patterning process and predict its responses to external perturbations.

b. Parameter Fitting and Stochastic Simulation

Based on parameters from previous literatures and fitted biologically feasible values, the PDE model can be numerically solved with Pdepe package (Mathworks), which has been used to solve initial-boundary value problems for systems of parabolic and elliptic PDEs in the one spatial variable x and time t. The model contains two parts, ODE part (Eqs 7-10) and PDE part (Eqs 9-12). First, ode45 package was used to solve the ODE term (U, A, Ci, Hi), with defined initial conditions (such as [1, 1, 1, 1]) and given parameter sets. Then, the bvp5c package was used to solve the solutions of U and A to solve the PDE part ($C_i$, $H_i$, $C_e$, $H_e$). Here, the range of x-axis is assumed to be large enough so that all variables are 0 at the boundary, thus the initial condition for the PDE part is [1, 1, 0, 0].

It is well known that the two diffusible signaling molecules with different diffusion constants are one of the fundamental requirements to generate Turing patterns (7-10). In the described system, C6 and C12 can be used to mediate the intercellular communication by diffusing in the colony and semi-solid medium. Previous studies indicate that the diffusion rates for C6 and C12 are very similar (less than 1.5-fold difference). Given that their similar chemical structures (C12 only has six more carbons than C6), they are assumed to have the same diffusion coefficient (Dn). The application of external inducers was also assumed to influence the original diffusion rates of C6 and C12 going through the cell membrane to some extent (owning to the limitation of cell membrane's molecule transport). For example, C6 addition on the medium leads to a slight decrease of diffusion rate of C12 through cell membrane (Dh), and vice versa (Table 3).

Figure 1E:
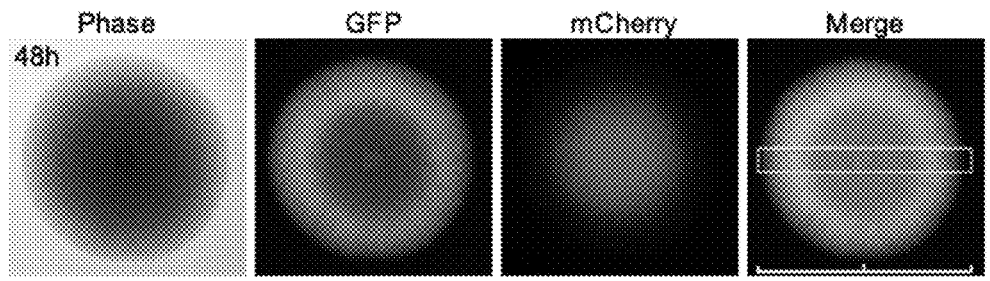
Figure 1F:
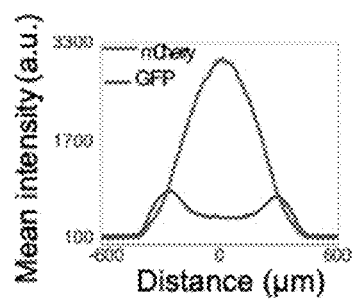
Figure 1G:
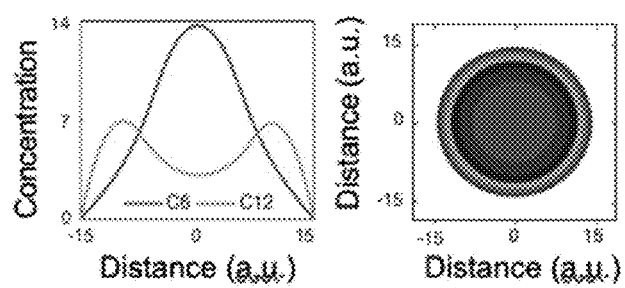

To mathematically explain the different ring patterns from the same MINPAC circuit in FIGS. 1E and 3A, it was inferred that the different patterns are likely due to the stochasticity of initial cellular state, which could be attributed to gene expression noise in the cells. The inherently stochastic transcription and translation processes and environmental fluctuations lead to variations of each gene expression, and even distinct phenotypes in single cells. In the model simulations, through changing the initial conditions for the four intracellular species LuxI, LasI, $C_i$ and $H_i$ (Table 2), the experimental results (FIGS. 1E and 3A) could successfully be recapitulated. The domain size (N) of each colony is also accordingly set to run the simulation.

For no induction scenarios, zero boundary conditions were used to solve the PDE. To predict the patterning responses under external C6 and C12 inductions, the boundary and initial conditions of the PDE model were changed to mimic such experimental perturbations. However, C6 and C12 application would also change the initial external C6 and C12 value (i.e. $C_e$ and $H_e$). So the boundary condition for $C_e$ and $H_e$ were set to [1, 0] and [0, 1] under C6 and C12 induction, respectively. In addition, since the external application of C6 and C12 further regulates the intracellular genes expression and MINPAC dynamics, so the initial values for LuxI, LasI, Ci and Hi were changed (Table 3) under these two scenarios. Experimental results showed a good match with the model predictions (FIGS. 3B, 10B, and 10C).

The induction of IPTG and aTc, on the other hand, tunes the strength of the mutual inhibition in MINPAC circuit. IPTG application counteracts LacI's inhibition on Plux/lac, leading to more LasI expression. By increasing the production rates of LasI ($k_2$) and internal C12 ($k_4$) in the model, a target-like mCherry ring with an outer GFP ring pattern was predicted, which is further verified by the experimental data (FIG. 3B). On the contrary, inducer aTc alleviates the repressor TetR's inhibition to Plas/tet transcription and promotes mCherry expression. So the production rates of LuxI ($k_2$) and internal C6 ($k_4$) in the model were decreased while the basal expression of Plas/tet ($b_1$) were increased. The prediction suggests that cells would have a dominant mCherry expression under aTc induction, which is also confirmed by experimental result (FIG. 10C).

Together, the reaction-diffusion model mostly recapitulated experimental results. The reaction-diffusion model also helped building understanding of the MINPAC-directed ring pattern formation process and predict the pattern formation from external perturbations. The environmental effects including space and nutrition limitations on cell growth and pattern formation were not considered in the modeling, even though it might improve the model's prediction efficacy.

c. Model Development for the Control Circuits

For the three control circuits of MINPAC in FIG. 4C, a similar strategy to model their molecular interactions was employed, because the control circuit were engineered with the same biological components. All three control circuits have C6 and C12 intracellular synthesis and extracellular diffusion processes, so the dynamics of $C_i$, $H_i$, $C_e$, and $H_e$ were the same as in the MINPAC model (Eqs 9-12). Thus, only the reaction equations for LuxI and LasI based on the specific circuit topology needed to be changed.

In the first control, the intercellular X-Y communication modules are replaced by intercellular auto-activations of X and Y (FIG. 4C, top), so the positive feedback terms in the LuxI (U) and LasI (A) equations were modified:

$$\frac{\partial U}{\partial t} = \beta_1 + \frac{k_1 \cdot (U \cdot C_i)^{n1}}{1 + (U \cdot C_i)^{n1}} \cdot \frac{1}{1 + A^{m1}} - d_1 \cdot U \quad \text{(Eq 13)}$$

$$\frac{\partial A}{\partial t} = \beta_2 + \frac{k_2 \cdot (A \cdot H_i)^{n2}}{1 + (A \cdot H_i)^{n2}} \cdot \frac{1}{1 + U^{m2}} - d_2 \cdot A \quad \text{(Eq 14)}$$

In the second control circuit, the mutual inhibition module is removed compared to the first control circuit, namely a circuit with two positive feedback motifs (FIG. 4C, middle). So the model can be written as:

$$\frac{\partial U}{\partial t} = \beta_1 + \frac{k_1 \cdot (U \cdot C_i)^{n1}}{1 + (U \cdot C_i)^{n1}} - d_1 \cdot U \quad \text{(Eq 15)}$$

$$\frac{\partial A}{\partial t} = \beta_2 + \frac{k_2 \cdot (A \cdot H_i)^{n2}}{1 + (A \cdot H_i)^{n2}} - d_2 \cdot A \quad \text{(Eq 16)}$$

The third control is a sub-network of MINPAC, where the mutual inhibition is removed but having all the other regulatory edges (FIG. 4C, bottom). So the model can be described as:

$$\frac{\partial U}{\partial t} = \beta_1 + \frac{k_1 \cdot (U \cdot H_i)^{n1}}{1 + (U \cdot H_i)^{n1}} - d_1 \cdot U \quad \text{(Eq 17)}$$

$$\frac{\partial A}{\partial t} = \beta_2 + \frac{k_2 \cdot (A \cdot C_i)^{n2}}{1 + (A \cdot C_i)^{n2}} - d_2 \cdot A \quad \text{(Eq 18)}$$

It is worth noting that although the parameter symbols in the three control circuits are the same to MINPAC model, their values may be different, especially for the production rates of LuxI ($k_1$) and LasI ($k_2$) as well as the promoter leakages ($b_1$ and $b_2$) because of the distinct architectures and molecular regulations on the promoters. For example, the basal expression in the second circuit (Control-II) should be larger than in the first circuit (Control-I) and MINPAC circuit owning to a lack of repressors and direct positive autoregulation from LuxR and LuxI. Specific parameters are listed in Table 4.

d. Traveling Wave Solution

MINPAC is composed of two topologically equivalent motifs where a self-activating node activates the other node and it in turn inhibits the self-activating node (FIG. 2A), each forming a robust positive-plus-negative oscillator topology. However, the two motifs in the MINPAC gene circuit might not be fully balanced. Results in FIGS. 5A and 5B show that the inhibition efficiency of LacI to promoter Plux/lac is lower than TetR to promoter Plas/tet.

According to a previous gene expression metric in polycistronic circuits, TetR expression in MINPAC circuit is 32.3% higher than LacI expression when Plux/lac and Plas/tet have the same production rate. Thus, the two motifs are likely to be unbalanced, indicating MINPAC could maintain a robust positive-plus-negative oscillator topology.

The simulations and experiment results suggest that the ring patterns observed are the outcomes of the spatiotemporal interaction of oscillatory dynamics owing to the network topology and the movement stemming from the diffusion process. After a short time, the solution of the reaction diffusion system approaches the form of a traveling wave. The traveling wave like solution will move forward at a speed asymptotically constant. If the speed is about one unit of length per unit of time, then the wave front resembles the mirror image of an oscillatory trajectory of the reaction system with a small initial value. A faster wave speed will stretch such oscillatory trajectory while a slower wave speed will compact it. The multiple peaks of such oscillatory trajectories give rise to the observed ring patterns.

Figure 2G:
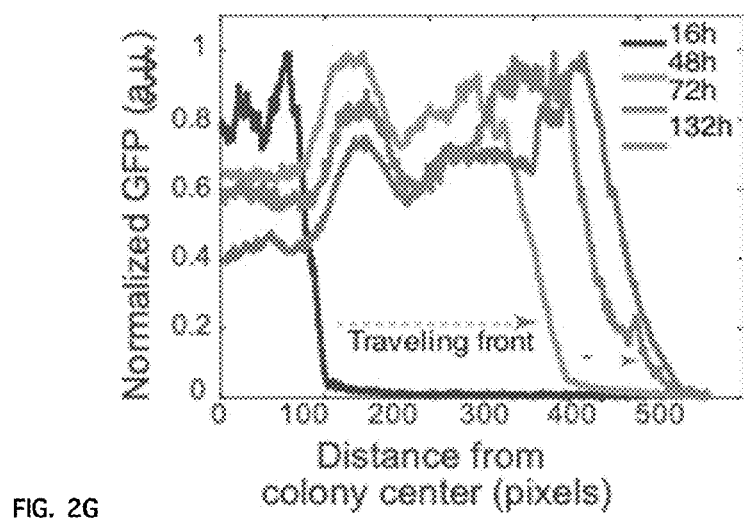

First, from the simulation result (the 3-D figure in FIG. 8B), the solution approximately takes the form of a traveling wave with a constant wave speed after a period of time (about t=100). The experiment results provide data for up to 132 hours only (FIG. 2F). As a result, one cannot observe a truly constant speed wave solution. Nevertheless, a traveling wave like solution emerges as time increases. Second, FIGS. 2E and 2G show that the simulation results match experiment observations qualitatively for a set of time points. Thus, the target-like ring patterns result from formation of oscillatory traveling-wave-like solutions in our RD models.

Tables

TABLE 1

Bio-components from Registry of standard biological parts.

| Biobrick number | Abbreviation | Description |
|---|---|---|
| BBa_K176009 | CP | Constitutive promoter family member J23107 actual sequence (pCon 0.36) |
| BBa_K182102 | Plux/lac | Hybrid promoter (followed by a RBS) activated by LuxR-C6 complex but inhibited by LacI protein |
| BBa_I14015 | Plas/tet | Hybrid promoter activated by LasR-C12 complex, but inhibited by TetR protein |
| BBa_B0034 | RBS | Ribosome binding site |
| BBa_B0015 | Terminator | Transcriptional terminator (double) |
| BBa_C0062 | LuxR | LuxR repressor/activator |
| BBa_C0179 | LasR | LasR activator |
| BBa_C0161 | LuxI | Autoinducer synthase for 3OC6HSL (3-oxohexanoyl-homoserine lactone, C6) from *Vibrio fischeri* |
| BBa_C0178 | LasI | Autoinducer synthase for 3OC12HSL (N-3-oxododecanoyl homoserine lactone, C12) from *Pseudomonas aeruginosa* |
| BBa_C0012 | LacI | LacI repressor from *E. coli* |
| BBa_C0040 | TetR | Tetracycline repressor from transposon Tn10 |
| BBa_J06702 | mCherry | mCherry (optimized monomeric red fluorescent protein) generator |
| BBa_E0040 | GFP | Green fluorescent protein |

TABLE 2

Parameters of the three cases for the MINPAC pattern formation under no inductions.

| Parameter | FIG. 1G | FIG. 3B (top) | FIG. 3B (bottom) |
|---|---|---|---|
| Initial condition | (1, 10, 6, 10) | (8, 4, 10, 1) | (1, 100, 60, 100) |
| M | 1000 | 1000 | 1000 |
| ex | 31 | 31 | 31 |
| N | 15 | 16.5 | 86.3 |
| d4 | 20 | 20 | 20 |
| d6 | 20 | 20 | 20 |
| Dh | 4 | 4 | 4 |
| Dc | 4 | 4 | 4 |

TABLE 2-continued

Parameters of the three cases for the MINPAC pattern formation under no inductions.

| Parameter | FIG. 1G | FIG. 3B (top) | FIG. 3B (bottom) |
|---|---|---|---|
| Dn | 800 | 800 | 800 |
| k1 | 640 | 640 | 640 |
| k2 | 700 | 700 | 700 |
| k3 | 80 | 80 | 80 |
| k4 | 105 | 105 | 105 |
| k5 | 1 | 1 | 1 |
| k6 | 1 | 1 | 1 |
| Kc | 70 | 70 | 70 |
| Kh | 82 | 82 | 82 |
| m1 | 4 | 4 | 4 |
| m2 | 4 | 4 | 4 |
| b1 | 0.8 | 0.8 | 0.8 |
| b2 | 0.5 | 0.5 | 0.5 |
| d1 | 1.19 | 1.19 | 1.19 |
| d2 | 1.19 | 1.19 | 1.19 |
| d3 | 0.56 | 0.56 | 0.56 |
| d5 | 0.8 | 0.8 | 0.8 |
| n1 | 2 | 2 | 2 |
| n2 | 4 | 4 | 4 |
| n3 | 3 | 3 | 3 |
| n4 | 2 | 2 | 2 |

TABLE 3

Parameters of the MINPAC prediction under four different inducers.

| Parameter | C6 induction (FIG. 4A Top) | IPTG induction (FIG. 4A Bottom) | C12 induction (FIG. 10B) | aTc induction (FIG. 10C) |
|---|---|---|---|---|
| Initial condition | (1, 1, 20, 1) | (2, 1, 1, 1) | (1, 1, 2, 18) | (1, 1, 1, 1) |
| M | 1000 | 1000 | 1000 | 1000 |
| ex | 31 | 31 | 31 | 31 |
| N | 62 | 39.5 | 58 | 19 |
| d4 | 20 | 20 | 20 | 20 |
| d6 | 20 | 20 | 20 | 20 |
| Dh | 3.5 | 3.5 | 4 | 3.5 |
| Dc | 4 | 3.5 | 3.5 | 3.5 |
| Dn | 800 | 800 | 800 | 800 |
| k1 | 640 | 640 | 640 | 640 |
| k2 | 700 | 850 | 700 | 300 |
| k3 | 80 | 80 | 80 | 80 |
| k4 | 105 | 128 | 105 | 80 |
| k5 | 1 | 1 | 1 | 1 |
| k6 | 1 | 1 | 1 | 1 |
| Kc | 70 | 70 | 70 | 70 |
| Kh | 82 | 82 | 82 | 82 |
| m1 | 4 | 4 | 4 | 4 |
| m2 | 4 | 4 | 4 | 4 |
| b1 | 0.8 | 0.4 | 0.8 | 2.6 |
| b2 | 0.5 | 0.45 | 0.5 | 0.5 |
| d1 | 1.19 | 1.19 | 1.19 | 1.19 |
| d2 | 1.19 | 1.19 | 1.19 | 1.19 |
| d3 | 0.56 | 0.56 | 0.56 | 0.56 |
| d5 | 0.8 | 0.8 | 0.8 | 0.8 |
| n1 | 2 | 2 | 2 | 2 |
| n2 | 4 | 4 | 4 | 4 |
| n3 | 3 | 3 | 3 | 3 |
| n4 | 2 | 2 | 2 | 2 |

TABLE 4

Parameters of the three control circuits.

| Parameter | Control I (FIG. 4C, Top) | Control II (FIG. 4C, Middle) | Control III (FIG. 4C, Bottom) |
|---|---|---|---|
| Initial condition | (1, 1, 1, 1) | (1, 1, 1, 1) | (1, 1, 1, 1) |
| M | 1000 | 1000 | 1000 |
| ex | 31 | 31 | 31 |
| N | 20 | 20 | 20 |
| d4 | 20 | 20 | 20 |
| d6 | 20 | 20 | 20 |
| Dh | 4 | 4 | 4 |
| Dc | 4 | 4 | 4 |
| Dn | 800 | 800 | 800 |
| k1 | 740 | 800 | 52 |
| k2 | 800 | 980 | 40 |
| k3 | 80 | 80 | 80 |
| k4 | 105 | 105 | 105 |
| k5 | 1 | 1 | 1 |
| k6 | 1 | 1 | 1 |
| Kc | 70 | 70 | 70 |
| Kh | 82 | 82 | 82 |
| m1 | 4 | — | — |
| m2 | 4 | — | — |
| b1 | 0.5 | 2.5 | 1 |
| b2 | 0.8 | 2.5 | 0.7 |
| d1 | 1.19 | 1.19 | 1.19 |
| d2 | 1.19 | 1.19 | 1.19 |
| d3 | 0.56 | 0.56 | 0.56 |
| d5 | 0.8 | 0.8 | 0.8 |
| n1 | 2 | 2 | 2 |
| n2 | 4 | 4 | 4 |
| n3 | 3 | 3 | 3 |
| n4 | 2 | 2 | 2 |

What is claimed is:

1. A plasmid comprising:
   a Plas/tet promoter;
   a Plux/lac promoter;
   a reporter gene; and
   a combination of genes selected from the group consisting: LacI, LuxI, LasR, LuxR, LasI, and TetR,
   wherein the Plas/tet promoter drives the expression of the reporter gene or the combination of genes; and the Plux/lac promoter drives the expression of the reporter gene or the combination of genes.

2. The plasmid of claim 1, wherein the combination of genes comprises:
   LacI or LuxR;
   LuxI or LasI; and
   LasR or TetR.

3. The plasmid of claim 1, wherein the combination of genes comprises:
   LuxI or LuxR; and
   LasR or LasI.

4. The plasmid of claim 1, wherein the reporter gene is mCherry or green fluorescent protein (GFP).

5. The plasmid of claim 1, wherein the combination of genes comprises LacI, LuxI, and LasR.

6. The plasmid of claim 5, wherein the Plas/tet promoter drives expression of the combination of genes and the Plux/lac promoter drives expression of the reporter gene.

7. The plasmid of claim 6, wherein the reporter gene is GFP.

8. The plasmid of claim 1, wherein the combination of genes comprises LuxR, LasI, and TetR.

9. The plasmid of claim 8, wherein the Plux/lac promoter drives expression of the combination of genes and the Plas/tet promoter drives expression of the reporter gene.

10. The plasmid of claim 9, wherein the reporter gene is mCherry.

11. A synthetic gene circuit for modeling complex patterns comprising:
a first plasmid comprising:
a first hybrid promoter, wherein the first hybrid promoter is activated by a first gene and inhibited by a second gene;
a second hybrid promoter, wherein the second hybrid promoter is activated by a third gene and inhibited by a fourth gene;
a first reporter gene, wherein the second hybrid promoter drives the expression of the first reporter gene; and
a first combination of genes comprising the first gene, the fourth gene, and a first autoinducer synthase gene; and
a second plasmid comprising:
a third hybrid promoter, wherein the third hybrid promoter is activated by the first gene and inhibited by the second gene;
a fourth hybrid promoter, wherein the fourth hybrid promoter is activated by the third gene and inhibited by the fourth gene;
a second reporter gene, wherein the third hybrid promoter drives the expression of the second reporter gene; and
a second combination of genes comprising the second gene, the third gene, and a second autoinducer synthase gene,
wherein:
the first hybrid promoter and the third hybrid promoter are the same hybrid promoters;
the second hybrid promoter and the fourth hybrid promoter are the same hybrid promoters;
the first reporter gene and the second reporter gene are different,
the first autoinducer synthase gene and the second autoinducer synthase gene are different,
the product of the first autoinducer synthase gene forms a complex with the product of the first gene to activate the first hybrid promoter and the third hybrid promoter, and
the product of the second autoinducer synthase gene forms a complex with the product of the third gene to activate the second hybrid promoter and the fourth hybrid promoter.

12. The synthetic gene circuit of claim 11, wherein the first plasmid comprises:
a first Plas/tet promoter;
a first Plux/lac promoter;
the first reporter gene; and
the first combination of genes comprises LacI, LuxI, and LasR,
wherein the first Plas/tet promoter drive the expression of the first reporter gene and the first Plux/lac promoter drive expression of the first combination of genes; and
a second plasmid comprising:
a second Plas/tet promoter;
a second Plux/lac promoter;
the second reporter gene; and
the second combination of genes comprises LuxR, LasI, and TetR,
wherein the second Plux/lac promoter drives the expression of the second reporter gene and the second Plas/tet promoter drives expression of the second combination of genes.

13. The synthetic gene circuit of claim 11, wherein the first reporter gene is GFP.

14. The synthetic gene circuit of claim 11, wherein the second reporter gene is mCherry.

15. A method of generating an expression pattern of a first reporter gene, the method comprising:
introducing into a cell a synthetic gene circuit comprising a first plasmid and a second plasmid to produce an altered cell, wherein:
the first plasmid comprises:
a first hybrid promoter, wherein the first hybrid promoter is activated by a first gene and inhibited by a second gene;
a second hybrid promoter, wherein the second hybrid promoter is activated by a third gene and inhibited by a fourth gene;
the first reporter gene, wherein the second hybrid promoter drives the expression of the first reporter gene; and
a first combination of genes comprising the first gene, the fourth gene, and a first autoinducer synthase gene; and
the second plasmid comprises:
a third hybrid promoter, wherein the third hybrid promoter is activated by the first gene and inhibited by the second gene;
a fourth hybrid promoter, wherein the fourth hybrid promoter is activated by the third gene and inhibited by the fourth gene;
a second reporter gene, wherein the third hybrid promoter drives the expression of the second reporter gene; and
a second combination of genes comprising the second gene, the third gene, and a second autoinducer synthase gene;
wherein:
the first hybrid promoter and the third hybrid promoter are the same hybrid promoters;
the second hybrid promoter and the fourth hybrid promoter are the same hybrid promoters;
the first reporter gene and the second reporter gene are different;
the first autoinducer synthase gene and the second autoinducer synthase gene are different;
the product of the first autoinducer synthase gene forms a complex with the product of the first gene to activate the first hybrid promoter and the third hybrid promoter; and
the product of the second autoinducer synthase gene forms a complex with the product of the third gene to activate the second hybrid promoter and the fourth hybrid promoter; and
providing to the altered cell a first inducer compound, wherein the first inducer compound is the inducer for the second autoinducer synthase gene.

16. The method of claim 15, wherein the expression pattern is a ring pattern and
the first plasmid comprises:
a first Plas/tet promoter;
a first Plux/lac promoter;
the first reporter gene; and
the first combination of genes comprises LacI, LuxI, and LasR,
wherein the first Plas/tet promoter drive the expression of the first reporter gene and the first Plux/lac promoter drive expression of the first combination of genes; and the second plasmid comprising:
- a second Plas/tet promoter;
- a second Plux/lac promoter;
- the second reporter gene; and
- the second combination of genes comprises LuxR, LasI, and TetR,
- wherein the second Plux/lac promoter drive the expression of the second reporter gene and the second Plas/tet promoter drive expression of the second combination of genes.

17. The method of claim 16, wherein the first inducer compound is C6 and the amount of the first inducer compound provided is $1\times10^{-8}$ M, the altered cell is cultured in the presence of the first inducer compound for at least 70 hours.

18. The method of claim 16, further comprising providing an IPTG to the altered cell.

19. The method of claim 18, wherein the concentration of IPTG is 10 UM and the altered cell is cultured in the presence of IPTG for at least 70 hours.

20. The method of claim 15, wherein the cell is *E. coli*.

* * * * *